US009576229B2

(12) United States Patent
Hosoya et al.

(10) Patent No.: US 9,576,229 B2
(45) Date of Patent: Feb. 21, 2017

(54) IMAGE FORMING APPARATUS AND DETECTION APPARATUS

(71) Applicant: CANON KABUSHIKI KAISHA, Tokyo (JP)

(72) Inventors: Shinji Hosoya, Naka-gun (JP); Takuya Mukaibara, Susono (JP); Kenichi Fujii, Suntou-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/441,972

(22) PCT Filed: Nov. 14, 2013

(86) PCT No.: PCT/JP2013/081332
§ 371 (c)(1),
(2) Date: May 11, 2015

(87) PCT Pub. No.: WO2014/097810
PCT Pub. Date: Jun. 26, 2014

(65) Prior Publication Data
US 2015/0278662 A1 Oct. 1, 2015

(30) Foreign Application Priority Data

Dec. 19, 2012 (JP) .................. 2012-277445
Dec. 19, 2012 (JP) .................. 2012-277447

(51) Int. Cl.
*G06K 15/02* (2006.01)
*G03G 15/00* (2006.01)
(Continued)

(52) U.S. Cl.
CPC ........... *G06K 15/1878* (2013.01); *G01N 21/55* (2013.01); *G03G 15/5058* (2013.01);
(Continued)

(58) Field of Classification Search
CPC G06K 15/1878; G01N 21/55; G03G 15/5058; G03G 2215/0161; G03G 2215/0164
(Continued)

(56) References Cited

U.S. PATENT DOCUMENTS 8,260,164 B2   9/2012  Masuda
8,331,813 B2   12/2012 Ozeki
(Continued)

FOREIGN PATENT DOCUMENTS

JP   03-209281 A   9/1991
JP   9-247452 A    9/1997
(Continued)

OTHER PUBLICATIONS

International Search Report and Written Opinion in PCT/JP2013/081332 dated Dec. 17, 2013.
(Continued)

*Primary Examiner* — Quang N Vo
(74) *Attorney, Agent, or Firm* — Fitzpatrick, Cella, Harper & Scinto

(57) ABSTRACT

An image forming apparatus includes a detector for detecting one of position and density information of a detection image based on a signal corresponding to a difference between a value of a detection signal corresponding to a first position of one of the detection image on an image carrier and a surface of the image carrier and an average value of a value of the detection signal corresponding to a second position on a downstream side with respect to the first position in a moving direction of the detection image and a value of the detection signal corresponding to a third position on an upstream side with respect to the first position in the moving direction during a time when the detection image formed on the image carrier passes through an irradiation region of an irradiation device.

14 Claims, 22 Drawing Sheets

(51) Int. Cl.
*G01N 21/55* (2014.01)
*H04N 1/60* (2006.01)

(52) U.S. Cl.
CPC ............ *G03G 2215/0161* (2013.01); *G03G 2215/0164* (2013.01)

(58) Field of Classification Search
USPC .............................................. 358/1.9; 399/49
See application file for complete search history.

(56) References Cited

U.S. PATENT DOCUMENTS

| | | | |
|---|---|---|---|
| 8,564,782 B2 | 10/2013 | Masuda | |
| 8,787,782 B2 | 7/2014 | Masuda | |
| 9,049,313 B2 | 6/2015 | Mukaibara et al. | |
| 2009/0074476 A1* | 3/2009 | Miyadera | G03G 15/0194 399/301 |
| 2010/0221025 A1* | 9/2010 | Takahashi | G03G 15/5058 399/49 |
| 2014/0226997 A1 | 8/2014 | Koyama et al. | |
| 2014/0308049 A1 | 10/2014 | Yamaguchi et al. | |
| 2015/0037057 A1 | 2/2015 | Masuda | |

FOREIGN PATENT DOCUMENTS

| | | |
|---|---|---|
| JP | 2003-076129 A | 3/2003 |
| JP | 2004-212577 A | 7/2004 |
| JP | 2004-361871 A | 12/2004 |
| JP | 2005-241933 A | 9/2005 |
| JP | 2005-300918 A | 10/2005 |
| JP | 2006-350383 A | 12/2006 |
| JP | 2009-258601 A | 11/2009 |
| JP | 2010-122463 A | 6/2010 |
| JP | 2010-180570 A | 8/2010 |
| JP | 2010-250049 A | 11/2010 |
| JP | 2011-175080 A | 9/2011 |
| JP | 2011-242441 A | 12/2011 |
| JP | 2012-037258 A | 2/2012 |
| JP | 2012-103567 A | 5/2012 |
| JP | 2012-181414 A | 9/2012 |
| JP | 2013-033181 A | 2/2013 |
| JP | 2013-068971 A | 4/2013 |
| JP | 2013-109319 A | 6/2013 |

OTHER PUBLICATIONS

Takuya Mukaibara Hidetoshi Hanamoto, U.S. Appl. No. 14/441,977, filed May 11, 2015.

* cited by examiner

F I G. 4A
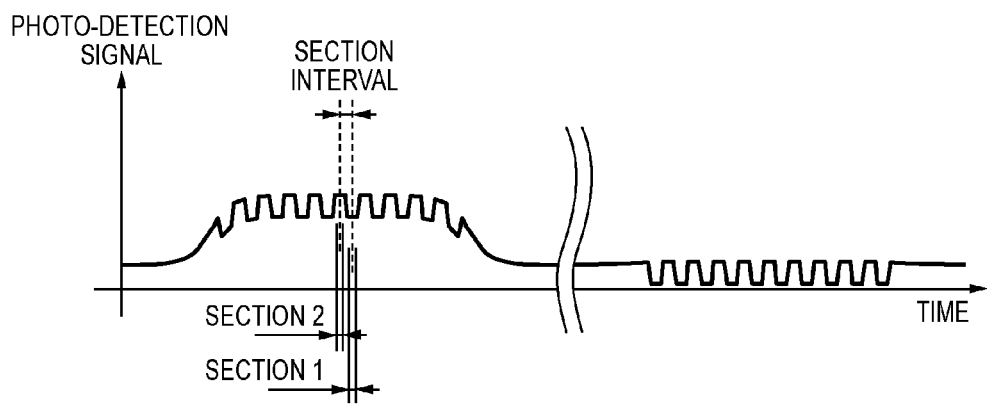
F I G. 4B
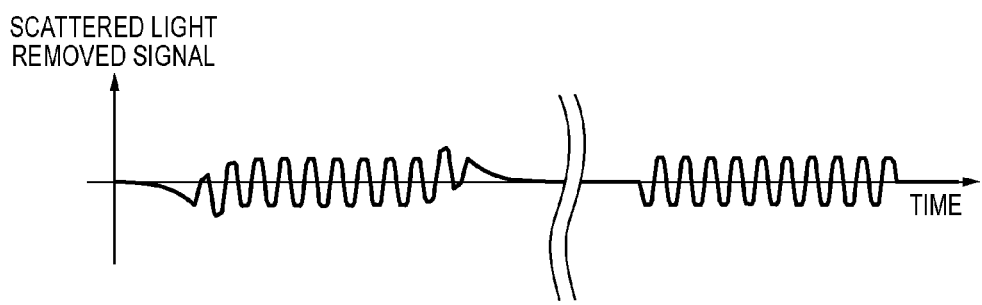
F I G. 4C
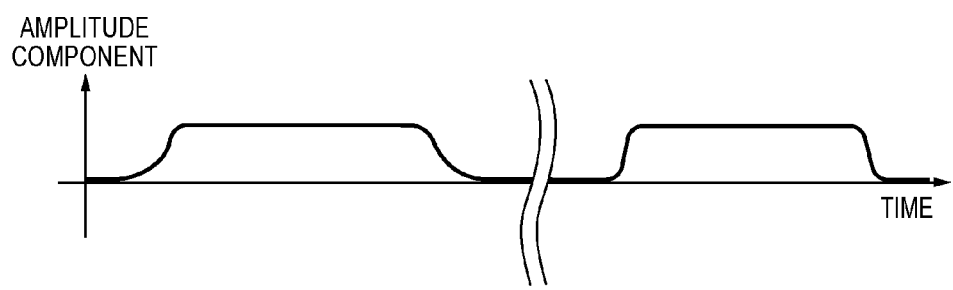

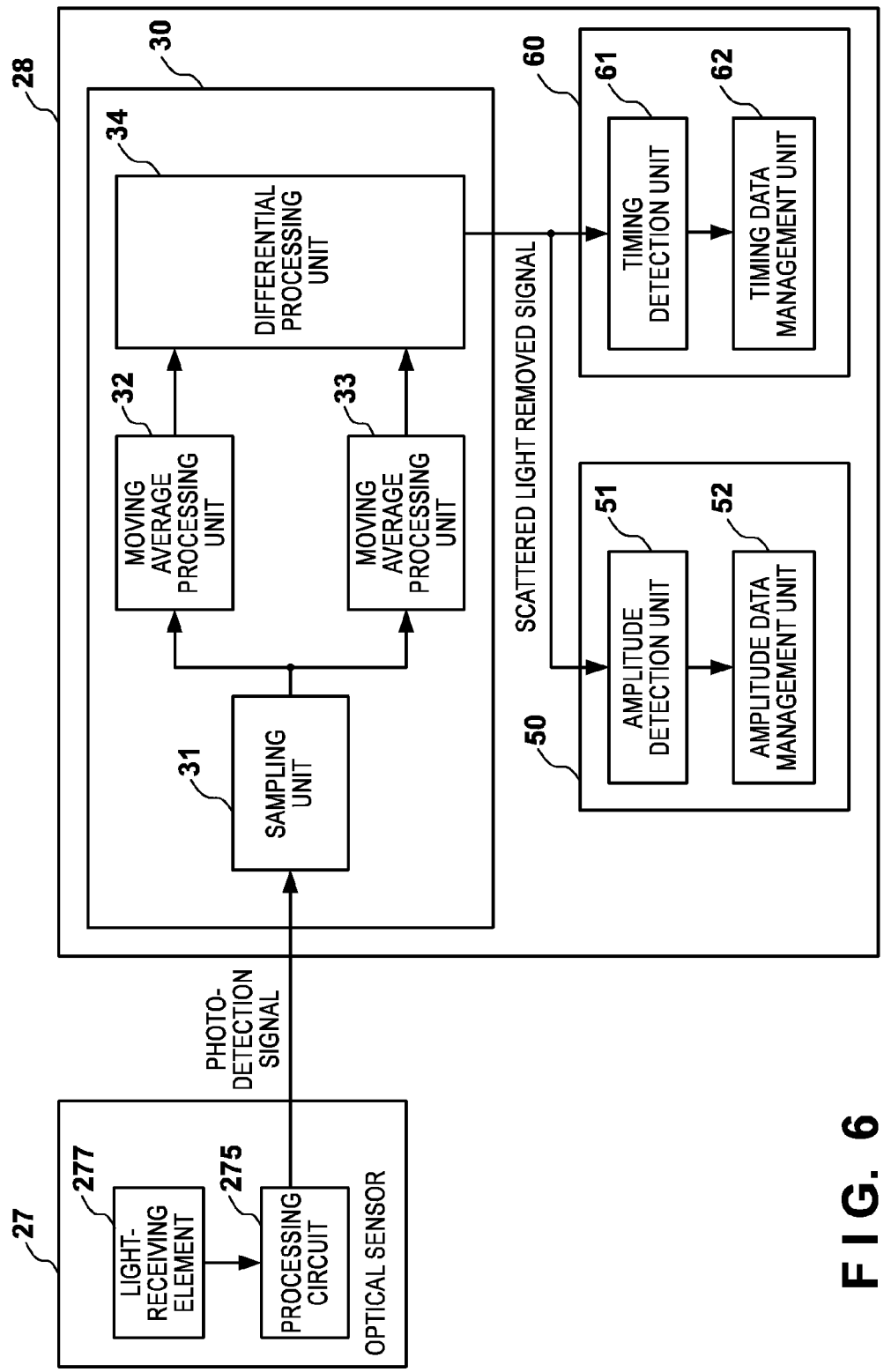
F I G. 6

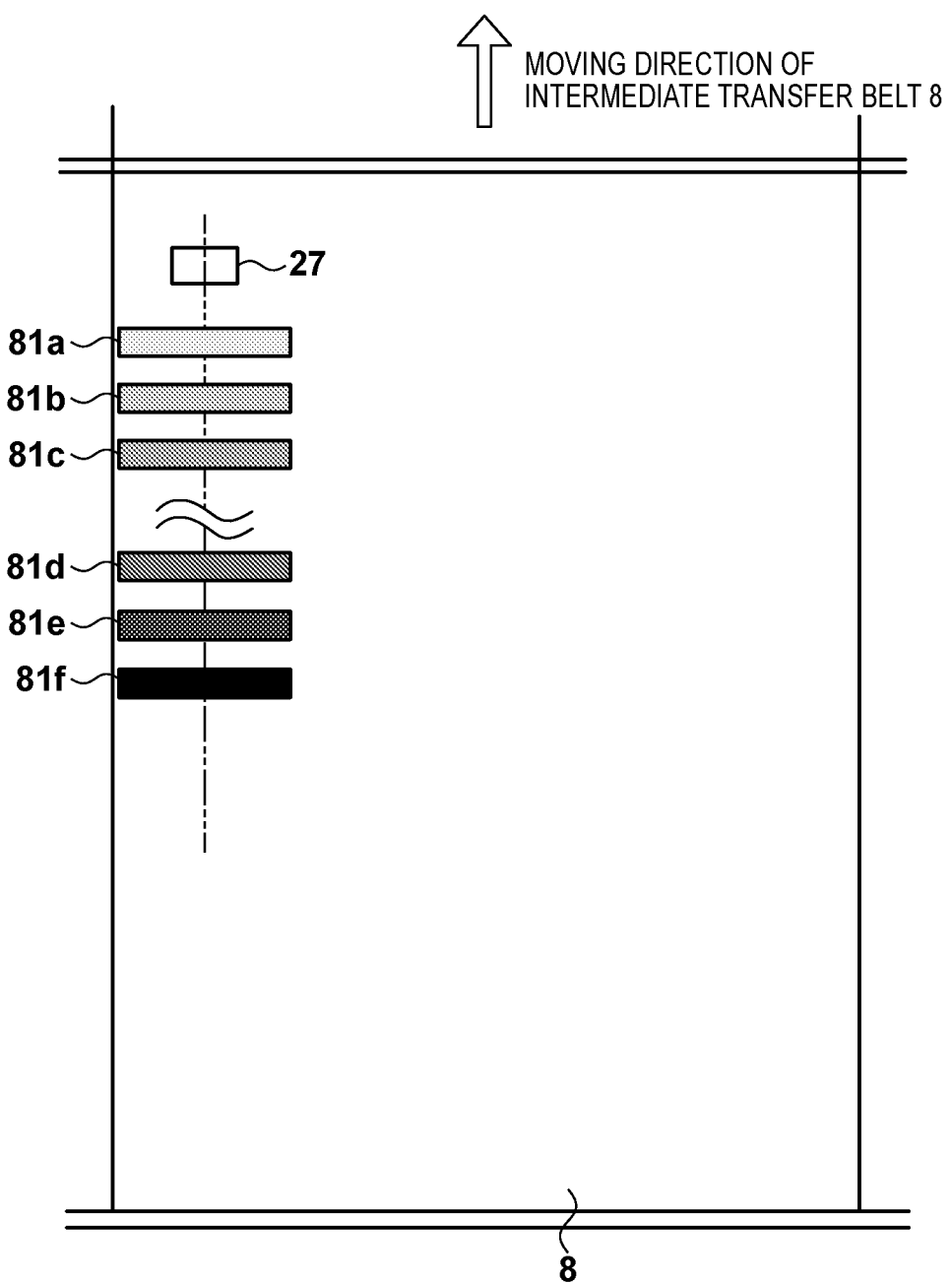

F I G. 13A    F I G. 13B    F I G. 13C
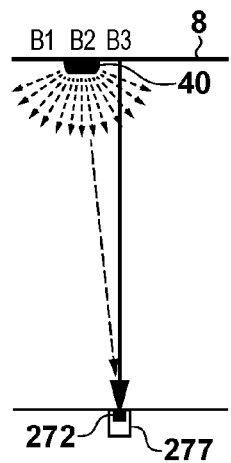 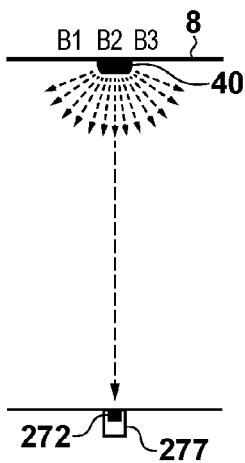 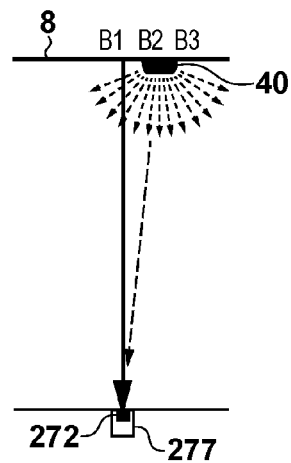
F I G. 13D    F I G. 13E    F I G. 13F
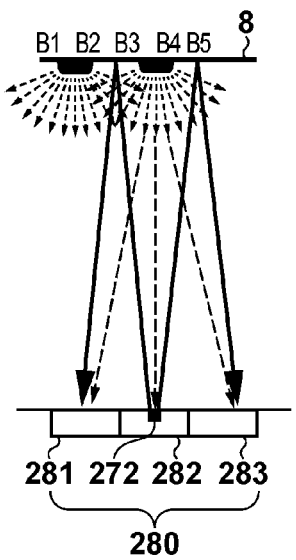 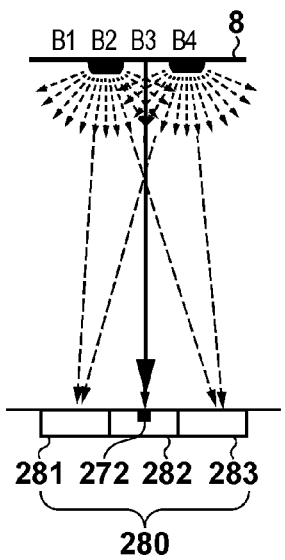 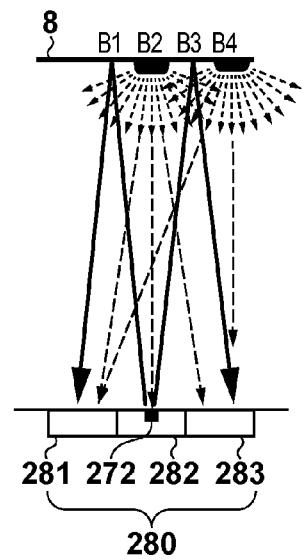

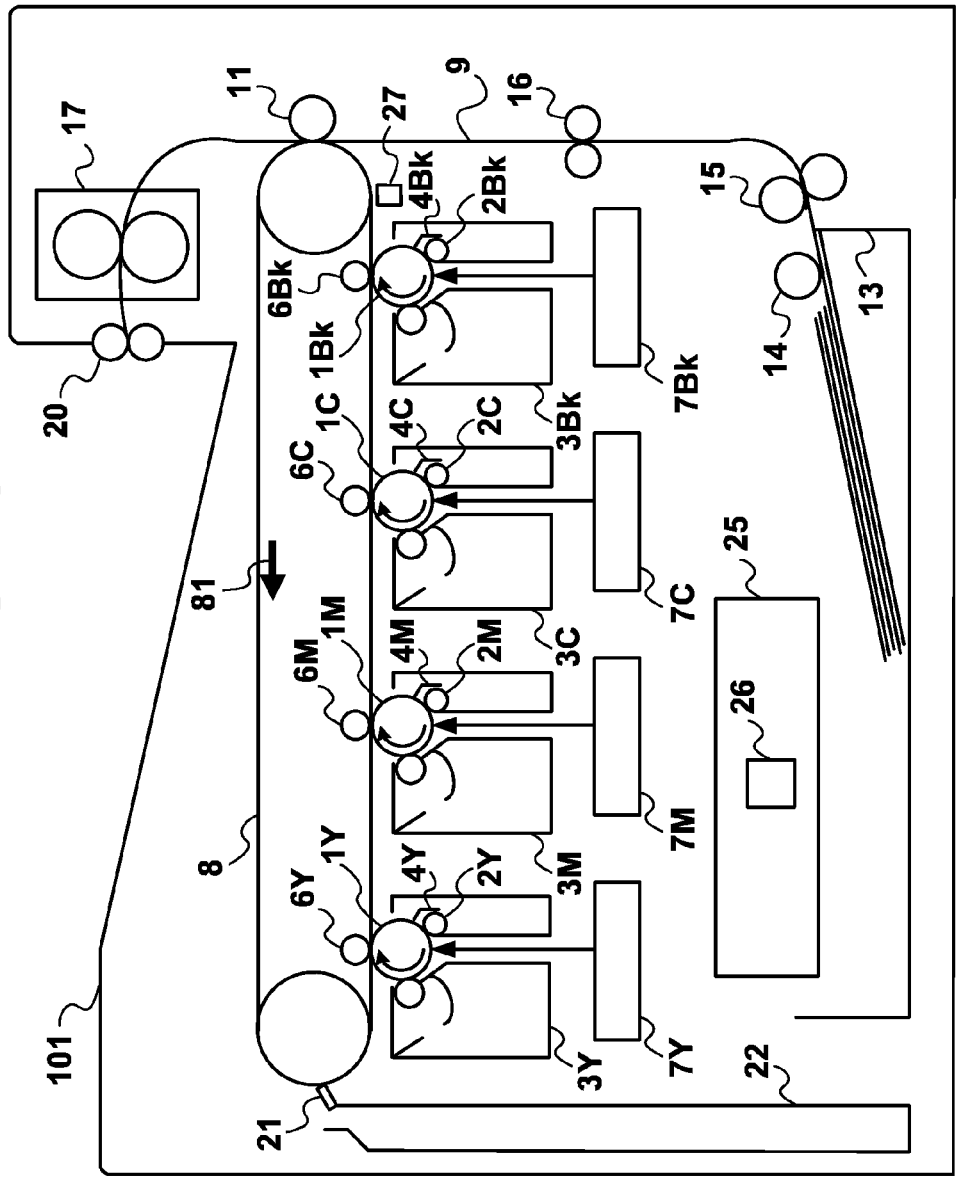

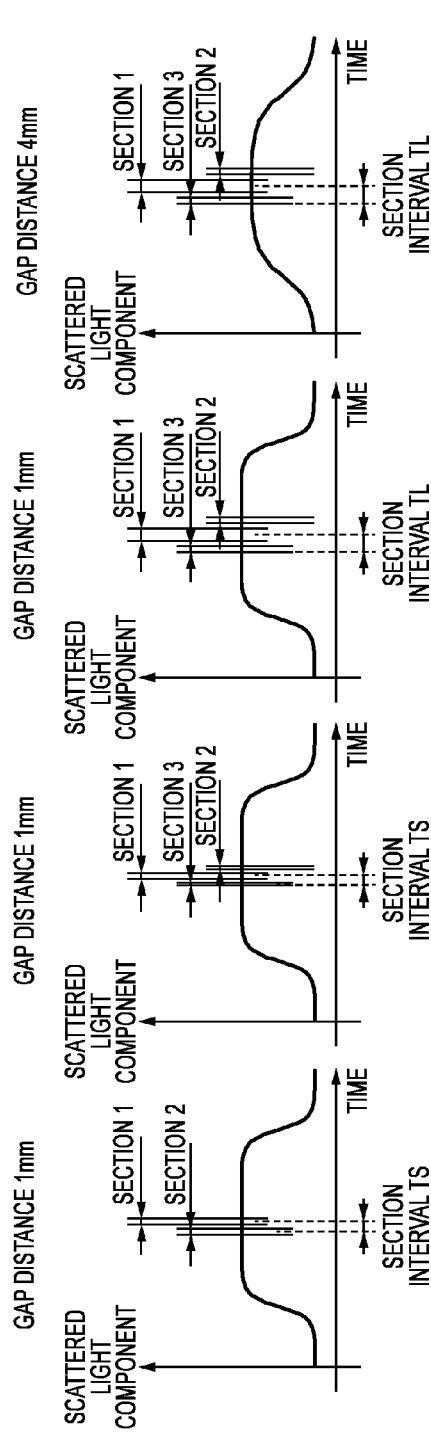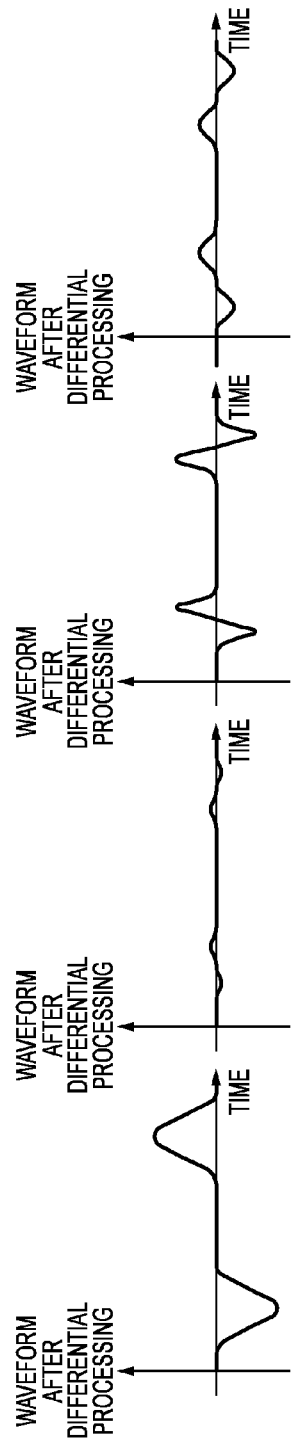

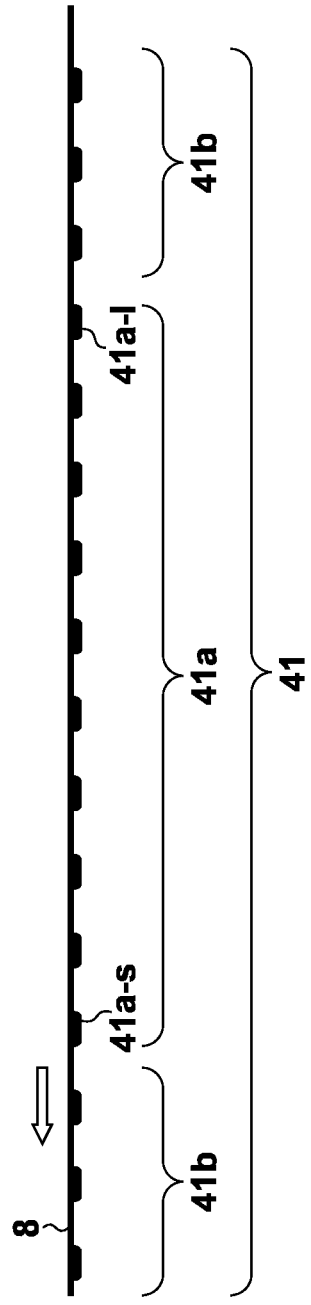
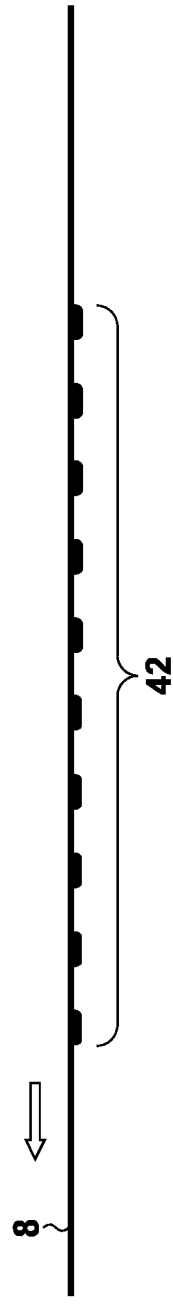
FIG. 18A
FIG. 18B

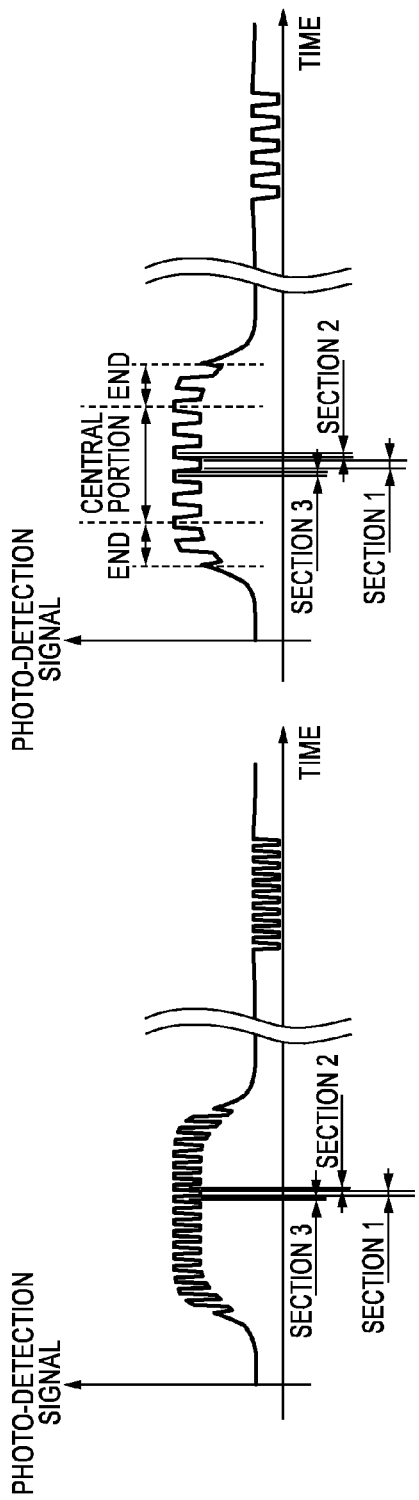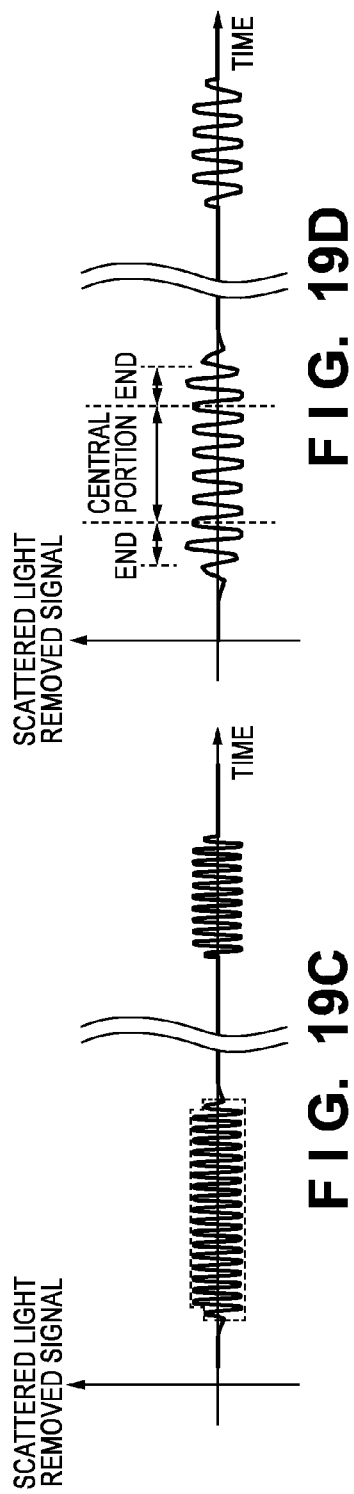

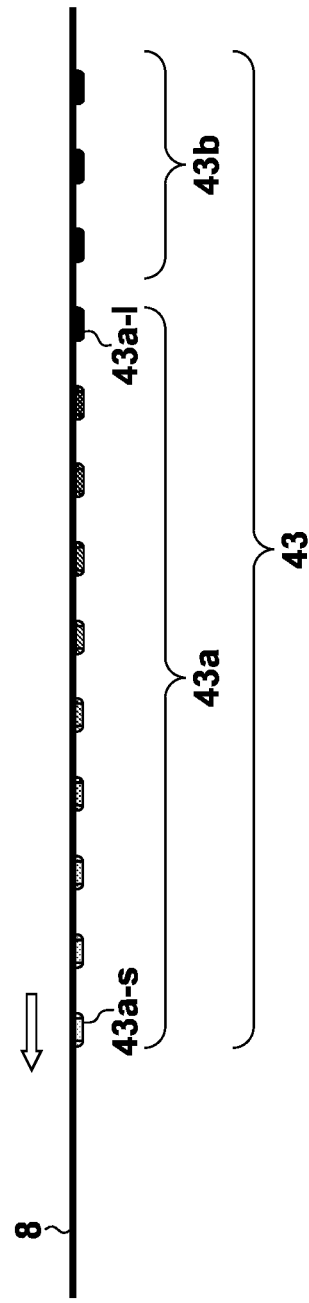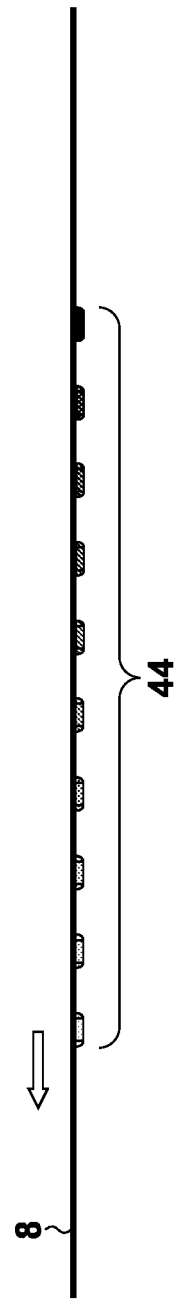

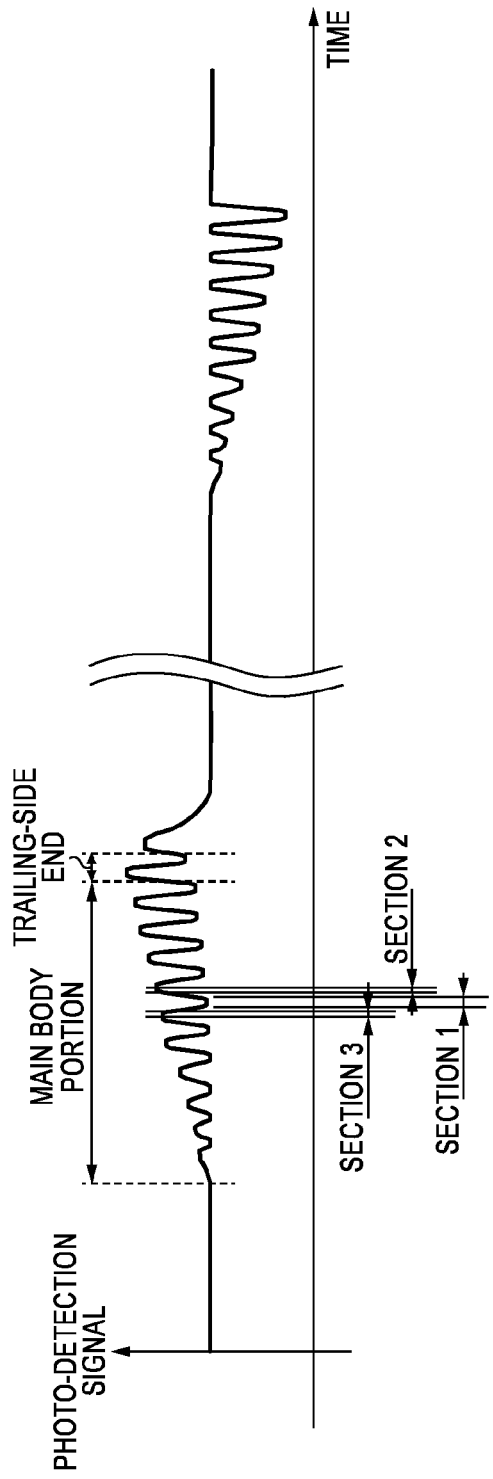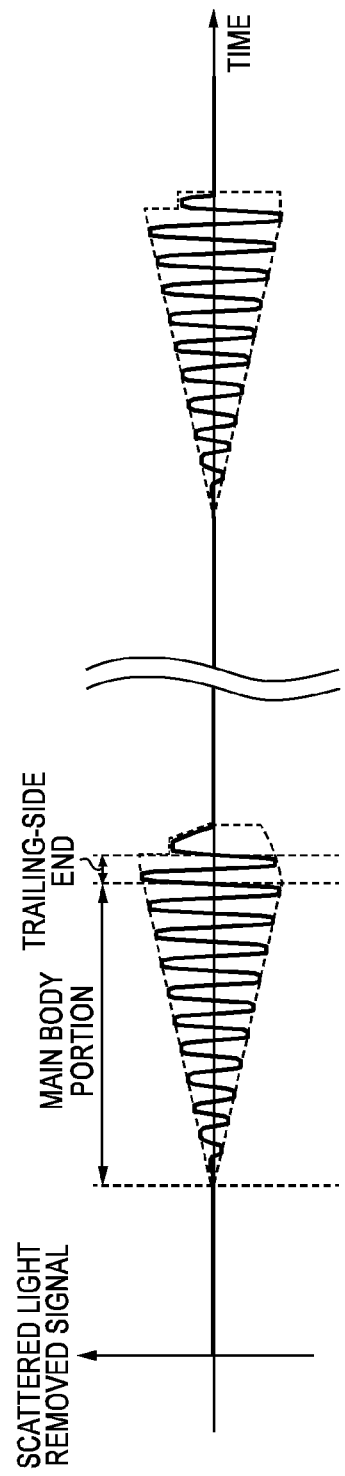

IMAGE FORMING APPARATUS AND DETECTION APPARATUS

TECHNICAL FIELD

The present invention relates to a color misalignment and density detection technique in an image forming apparatus such as a color laser printer, a color copying machine, and a color facsimile apparatus mainly using an electrophotographic process.

BACKGROUND ART

The mainstream of recent electrophotographic image forming apparatuses is a tandem type that provides a photosensitive member for each color to speed up printing. In the tandem-type image forming apparatus, for example, a detection image that is a developing material image used to detect a color misalignment or density is formed on an intermediate transfer belt. The color misalignment or density is corrected by detecting reflected light from the detection image using an optical sensor.

Japanese Patent Laid-Open No. 1991-209281 discloses providing two optical sensors that respectively detect specular-reflected light (to also be referred to as mirror-reflected light) and scatter-reflected light from a toner image and controlling the image density in accordance with the output difference between the two optical sensors. Japanese Patent Laid-Open No. 2003-76129 discloses an optical sensor that detects both specular-reflected light and scatter-reflected light using a prism. In these methods, one light-receiving element detects only the scatter-reflected light components, and correction is performed by, for example, subtracting the scatter-reflected light from the sum of the scatter-reflected light and specular-reflected light detected by the other light-receiving element, thereby extracting only the specular-reflected light components. In a method of detecting the density from the extracted specular-reflected light components, not the scatter-reflected light from the toner but the specular-reflected light from the background is mainly detected. Hence, the density can be detected independently of the color of the developing material that generates a difference in the scatter-reflected light amount. It is also supposedly possible to attain a high detection capability for a highlight region that is sensitive to the human visual characteristic. In the method of Japanese Patent Laid-Open No. 1991-209281, however, the error in correction processing of extracting only the specular-reflected light components becomes large. Japanese Patent Laid-Open No. 2005-300918 discloses reducing the effective spot diameter of specular-reflected light to lower the ratio of scatter-reflected light and thus improving the accuracy.

Consumption of the developing material by the detection image for color misalignment or density detection is required to be as low as possible. That is, the detection image is preferably made as small as possible. Even for a small detection image, a sensor having a high spatial resolution is necessary to accurately detect the density. Japanese Patent Laid-Open No. 2005-241933 discloses a sensor having a smaller irradiation area on the light emission side.

When the spot diameter of specular-reflected light is reduced in the conventional optical sensor, a variation of the LED chip position in the optical sensor or a mechanical variation of the converging mechanism greatly affects the yield in the manufacture or the detection accuracy. For example, to raise the spatial resolution of the optical sensor, the converging mechanism needs to be small. However, according to Japanese Patent Laid-Open No. 2005-241933, the spot diameter of the specular-reflected light is limited to about 1 mm when the variation in the manufacture and the like are taken into consideration.

SUMMARY OF INVENTION

According to one aspect of the present invention, an image forming apparatus includes: an image carrier; forming means for forming a detection image made of a developing material on the image carrier; irradiation means for irradiating the image carrier having the formed detection image with light; light-receiving means for receiving reflected light of the light irradiated by the irradiation means and outputting a detection signal corresponding to a light-receiving amount of the reflected light including a specular-reflected light component; and detection means for detecting one of position information and density information of the detection image based on a signal corresponding to a difference between a value of the detection signal corresponding to a first position of one of the detection image on the image carrier and a surface of the image carrier with the detection image formed and an average value of a value of the detection signal corresponding to a second position on a downstream side with respect to the first position in a moving direction of the detection image and a value of the detection signal corresponding to a third position on an upstream side with respect to the first position in the moving direction of the detection image during a time when the detection image formed on the image carrier passes through an irradiation region of the irradiation means.

Further features of the present invention will become apparent from the following description of exemplary embodiments with reference to the attached drawings.

BRIEF DESCRIPTION OF DRAWINGS

FIGS. 4A to 4C are explanatory views of processing for the detection image including a plurality of lines according to an embodiment;

FIG. 6 is a block diagram showing the schematic arrangement of a detection system according to an embodiment;

FIG. 10 is a view showing a detection image including lines of a plurality of halftone densities according to an embodiment;

FIGS. 13A to 13F are explanatory views of the differences between the fifth embodiment and other embodiments;

FIG. 16 is a sectional view showing the schematic arrangement of an image forming apparatus according to an embodiment;

FIGS. 17A to 17H are explanatory views of scatter-reflected light component removal;

FIGS. 18A and 18B are views showing detection images according to an embodiment;

FIGS. 19A to 19D are explanatory views of differential processing according to an embodiment;

FIGS. 20A and 20B are views showing detection images according to an embodiment;

FIGS. 22A and 22B are views showing a photo-detection signal and a scattered light removed signal according to an embodiment.

DESCRIPTION OF EMBODIMENTS

Figure 1A:
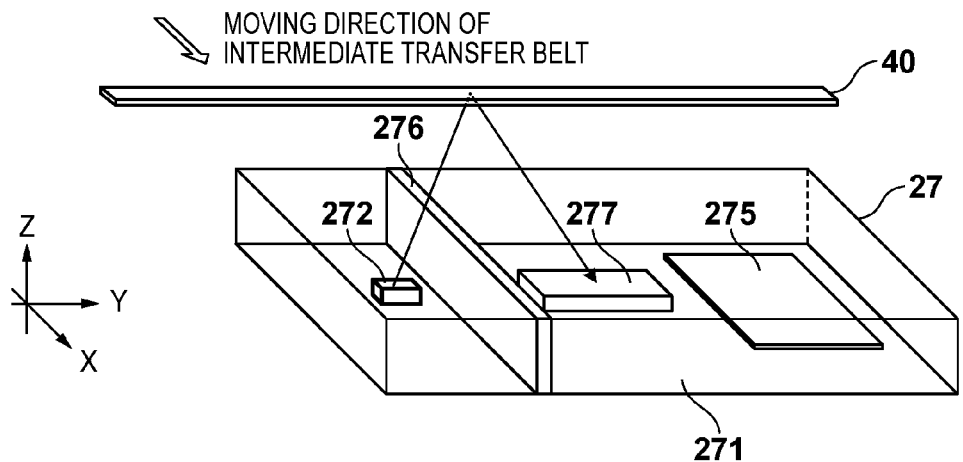
FIGS. 1A to 1C are views showing an optical sensor and a detection image including one line according to an embodiment.

Exemplary embodiments of the present invention will now be described with reference to the accompanying drawings. Note that the constituent elements unnecessary for the description of the embodiments are not illustrated in the following drawings. The same reference numerals denote the similar constituent elements throughout the drawings.

First Embodiment

An image forming apparatus 101 according to this embodiment will be described first with reference to FIG. 16. Note that the suffixes Y, M, C, and Bk of the reference numerals in FIG. 16 indicate that toners serving as developing materials for the corresponding members are yellow, magenta, cyan, and black, respectively. Note that reference numerals without the suffixes Y, M, C, and Bk are used when the colors need not be distinguished in the following description. A charging unit 2 uniformly charges a photosensitive member 1 serving as an image carrier rotated in the direction of an arrow in FIG. 16. An exposure unit 7 irradiates the photosensitive member 1 with a laser beam to form an electrostatic latent image on it. A developing unit 3 supplies a developing material to the electrostatic latent image by applying a developing bias and changes the electrostatic latent image to a toner image (developing material image) that is a visible image. A primary transfer roller 6 transfers the toner image on the photosensitive member 1 to an intermediate transfer belt 8 by a primary transfer bias. Note that the intermediate transfer belt 8 is rotated in the direction of an arrow 81. The photosensitive members 1 transfer the toner images to the intermediate transfer belt 8 in a superimposed manner, thereby forming a color image. A cleaning blade 4 removes the toner remaining on the photosensitive member 1 without being transferred to the intermediate transfer belt 8.

Conveyance rollers 14, 15, and 16 convey a recording medium in a cassette 13 to a secondary transfer roller 11 along a conveyance path 9. The secondary transfer roller 11 transfers the toner image on the intermediate transfer belt 8 to the recording medium by a secondary transfer bias. Note that the toner remaining on the intermediate transfer belt 8 without being transferred to the recording medium is removed by a cleaning blade 21 and collected by a waste toner collection container 22. A fixing unit 17 heats and pressurizes the recording medium with the transferred toner image to fix the toner image. The recording medium is then discharged by conveyance rollers 20 out of the apparatus. Note that an engine control unit 25 includes a microcontroller 26 and performs sequence control of various kinds of driving sources (not shown) of the image forming apparatus or various kinds of control using sensors. An optical sensor 27 is provided at a position facing the intermediate transfer belt 8.

For example, in a tandem-type image forming apparatus, the mechanical dimensions deviate from the design values due to assembly errors, part tolerance, thermal expansion of parts, and the like upon manufacturing the apparatus, resulting in displacement for each color. Hence, a detection image used to detect the color misalignment of each color is formed on the intermediate transfer belt 8 or the like, and reflected light from the formed detection image is detected by the optical sensor 27. The print start positions in the main scanning direction and sub-scanning direction and the image clock are adjusted for each color based on the detection result, thereby correcting the color misalignment. Additionally, in the image forming apparatus, the tint, density, and the like of the output image may change due to temporal changes or continuous printing. To correct this variation, density control is performed. In the density control, the detection image used to detect the density of each color is formed on the intermediate transfer belt 8 or the like, and reflected light from the formed detection image is detected by the optical sensor 27. The detection result is fed back to each voltage condition or a process formation condition such as laser power, thereby correcting the maximum density or halftone characteristic of each color. Density detection by the optical sensor 27 is generally done using a method of irradiating the detection image with a light source and detecting the intensity of reflected light by a light-receiving element. A signal corresponding to the intensity of the reflected light is processed by the microcontroller 26 and fed back to the process formation conditions. Maximum density control aims at maintaining predetermined color balance between colors and preventing spattering or a fixing failure of a color-overlaid image caused by excessive toner application. On the other hand, halftone control aims at preventing natural image formation from failing due to the shift of the output density with respect to the input image signal caused by a nonlinear input/output characteristic.

Details of the optical sensor 27 according to this embodiment will be described below with reference to FIG. 1A. FIG. 1A is a perspective view showing the relationship between the optical sensor 27 and a detection image 40. Note that the detection image 40 shown in FIG. 1A is a toner image made of a toner and including one line in a direction perpendicular to the moving direction of the intermediate transfer belt 8. Note that although the one line will be explained as a solid line in the following embodiment, it may be a discontinuous line such as a dotted line or a broken line. For the sake of illustrative simplicity, the intermediate transfer belt 8 itself is not illustrated in FIG. 1A. The optical sensor 27 according to this embodiment includes a light-emitting element 272, a light-receiving element 277, a processing circuit 275, and a light blocking wall 276 arranged on a package board 271. A normal light-emitting element used to detect color misalignment and density incorporates a reflecting plate to collect light diffused like a flare from the light-emitting element. A shell-shaped light-emitting element includes a condenser lens as well. On the other hand, the optical sensor 27 according to this embodiment includes neither a reflecting plate nor a condenser lens but only an LED chip, thereby irradiating the intermediate transfer belt 8 with divergent beams of a point source. The element on the light-receiving side similarly uses no condenser lens but, for example, a photodiode that outputs a current corresponding to a light-receiving amount. That is, reflected light from the intermediate transfer belt 8 is converted by the light-receiving element into a current corresponding to the light-receiving amount without passing through an optical member configured to converge or condense the light. The processing circuit 275 performs control of the light-emitting element 272 and processing of the signal detected by the light-receiving element 277, and outputs the processed signal to the microcontroller 26. Note that the optical sensor 27 is packaged by a resin and glass. The light blocking wall 276 is provided to prevent light emitted by the light-emitting element 272 from entering the light-receiving element 277 directly as stray light or after being reflected by the interface of the package.

The image forming apparatus causes the light-emitting element 272 to irradiate the intermediate transfer belt 8 and the detection image 40 formed on the intermediate transfer belt 8 with light and the light-receiving element 277 to receive reflected light from them, thereby detecting color misalignment and density. Basically, the color misalignment amount is detected by detecting the relative pass timing of the detection image 40 of each color. The density is determined by detecting the average light amount from the detection image 40 formed in halftone. The color misalignment and density are detected by monitoring the specular-reflected light components from the intermediate transfer belt 8. The image forming apparatus according to this embodiment uses four color toners. The light absorption/reflection characteristic changes depending on the toner color. For example, infrared light is mostly absorbed by the black toner and scatter-reflected by the toners of the remaining colors. Red light is mostly absorbed by the black and cyan toners and scatter-reflected by the toners of the remaining colors.

That is, it is necessary to perform processing of removing the scattered light components by the detection image 40 in a state in which the toners that generate a large amount of scatter-reflected light and the toners that less or hardly generate scatter-reflected light. To do this, in conventional color misalignment or density control, the optical sensor includes a converging mechanism, and a light-receiving element configured to detect only the scatter-reflected light components is separately provided. However, the optical sensor 27 of this embodiment includes no converging mechanism, and removes the scatter-reflected light components by the detection image 40. The optical sensor 27 of this embodiment includes no converging mechanism and can therefore be downsized to a fraction of the conventional size.

Figure 1B:
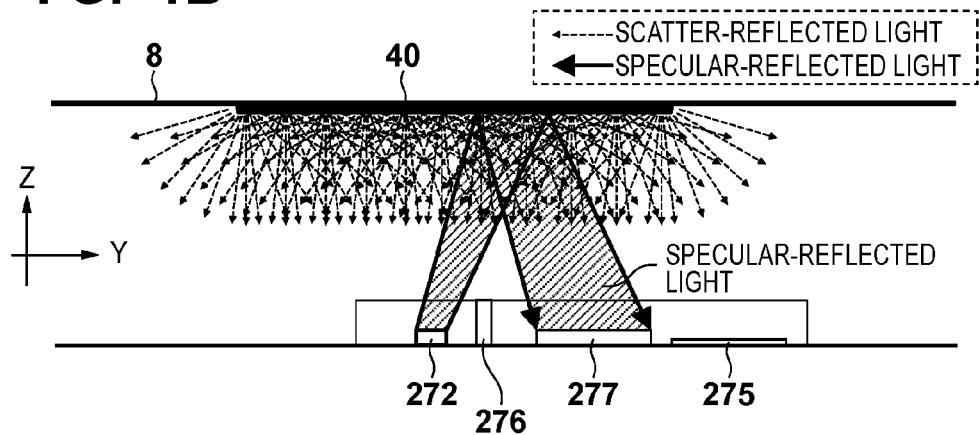
Figure 1C:
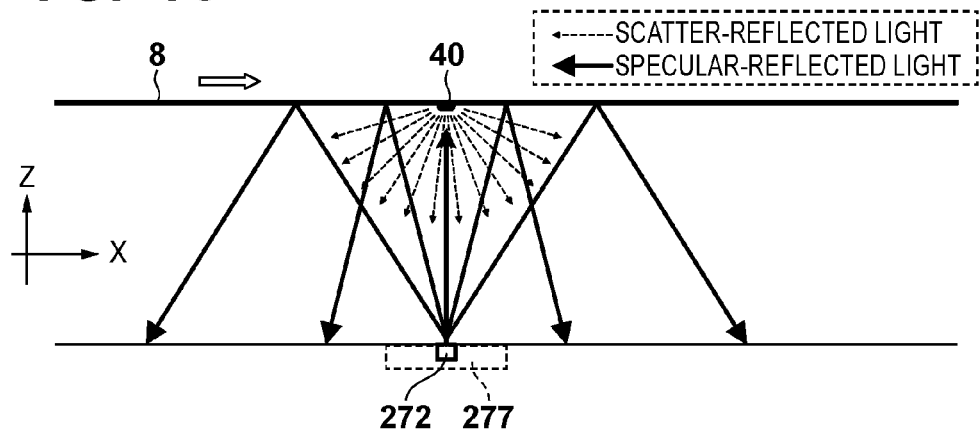

The state of reflected light from the intermediate transfer belt 8 and the detection image 40 on the intermediate transfer belt will be described below in detail with reference to FIGS. 1B and 1C. FIG. 1B is a view from the X-axis direction of FIG. 1A. The intermediate transfer belt 8 travels from the far side to the near side in the drawing. FIG. 1C is a view from the Y-axis direction of FIG. 1A. The intermediate transfer belt 8 travels in the direction of a hollow arrow in the drawing. Light emitted by the light-emitting element 272 is mainly specular-reflected by the surface of the intermediate transfer belt 8 and detected by the light-receiving element 277. This specular-reflected light is indicated by the solid arrows. Note that when the light-emitting element 272 is a point source, and the arrangement relationship makes the optical path length of the incident light to the intermediate transfer belt 8 and that of reflected light equal to each other, the width of the reflected light that enters the light-receiving element 277 is twice larger than the length on the intermediate transfer belt, as shown in FIG. 1B. On the other hand, the light emitted by the light-emitting element 272 is mainly scatter-reflected by the toner line of the detection image 40 formed on the intermediate transfer belt 8, and detected by the light-receiving element 277. This scatter-reflected light is indicated by the broken arrows. Note that as for the scatter-reflected light, the irradiation light from the light-emitting element 272 to the intermediate transfer belt 8 is not illustrated to avoid cumbersomeness, and the reflected light is indicated by short broken arrows.

Figure 2:
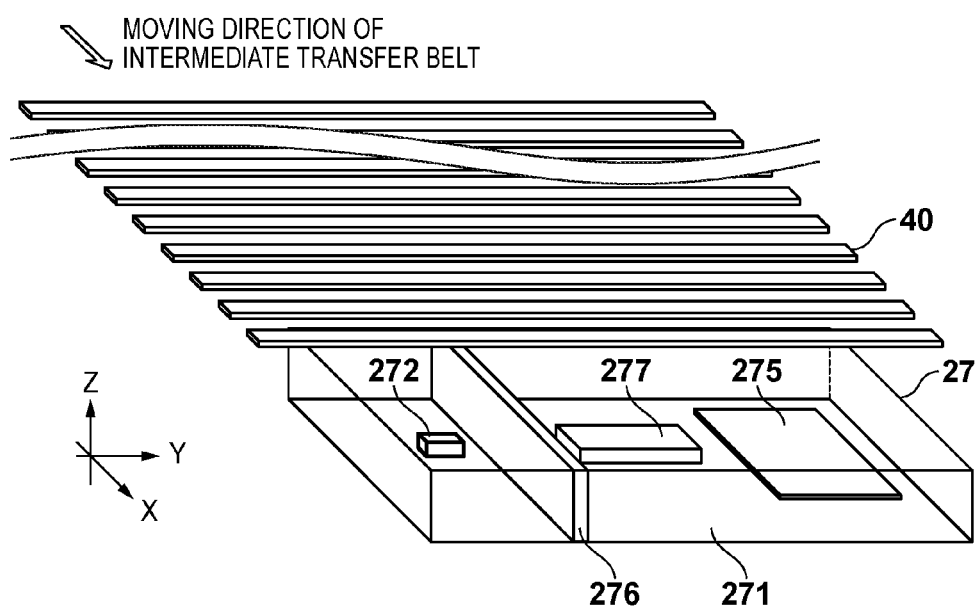
FIG. 2 is a perspective view showing the optical sensor and the detection image including a plurality of lines according to an embodiment.

The light-receiving amount of the optical sensor 27, that is, the photo-detection signal output from the optical sensor 27 when the striped detection image 40 including a plurality of lines is used will be described next with reference to FIGS. 2 and 3A to 3D. Note that although the lines will be explained as solid lines, they may be discontinuous lines such as dotted lines or broken lines. FIG. 2 is a perspective view showing the optical sensor 27 and the detection image 40 including a plurality of lines of toners in a direction perpendicular to the moving direction of the intermediate transfer belt 8. Note that for the sake of illustrative simplicity, the intermediate transfer belt 8 itself is not illustrated in FIG. 2 as well. FIGS. 3A to 3D are graphs showing time-rate changes in the light-receiving amount of the light-receiving element 277 when the detection image 40 including the plurality of lines passes through the irradiation region of the light-emitting element 272. Note that the detection image 40 has a width of about 100 mm in the sub-scanning direction, that is, in the moving direction of the intermediate transfer belt 8. FIGS. 3A to 3D show time-rate changes in the light-receiving amount when the width of each line and the width of the region (to be referred to as a space hereinafter) between adjacent lines are set to different values. More specifically, the line width and space width are minimum in FIG. 3A, and increase in the order of FIGS. 3B, 3C, and 3D. Note that FIGS. 3A to 3D illustrate the toner lines and spaces under the waveforms for the sake of reference. The leftward/rightward direction of the drawings corresponds to the sub-scanning direction. FIGS. 3A to 3D show not only the total amount of light received by the light-receiving element 277 but also the scatter-reflected light amount thereof.

Figure 3A:
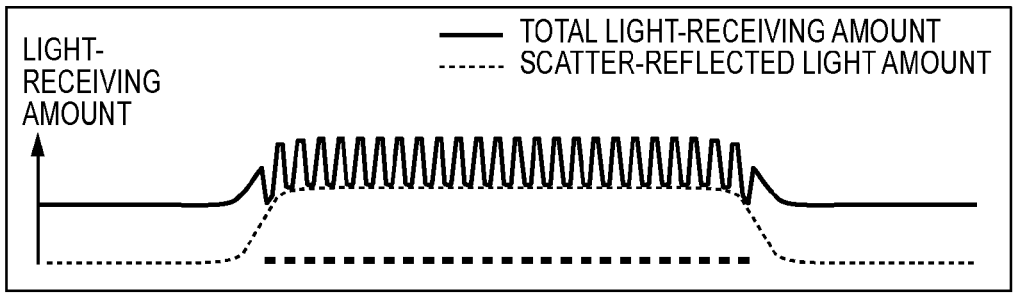
FIGS. 3A to 3D are graphs showing time-rate changes in the light-receiving amount upon detecting the detection image including a plurality of lines according to an embodiment.
Figure 3B:
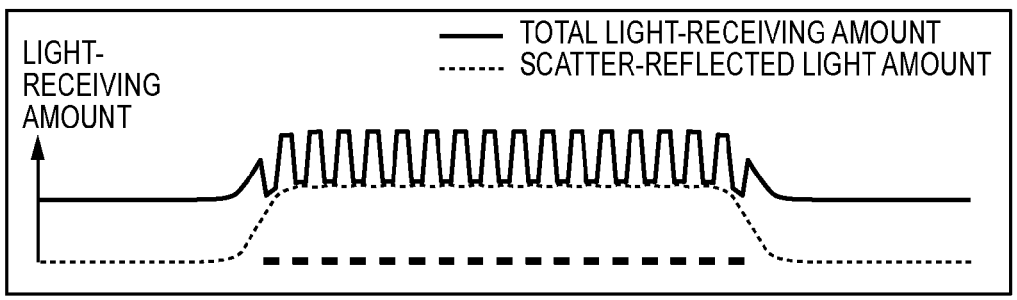
Figure 3C:
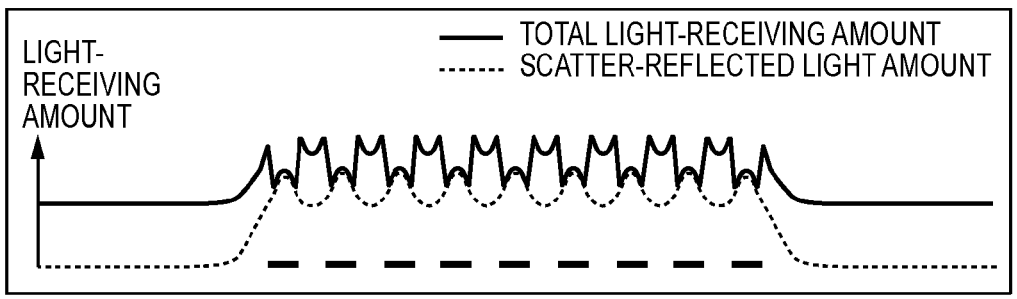
Figure 3D:
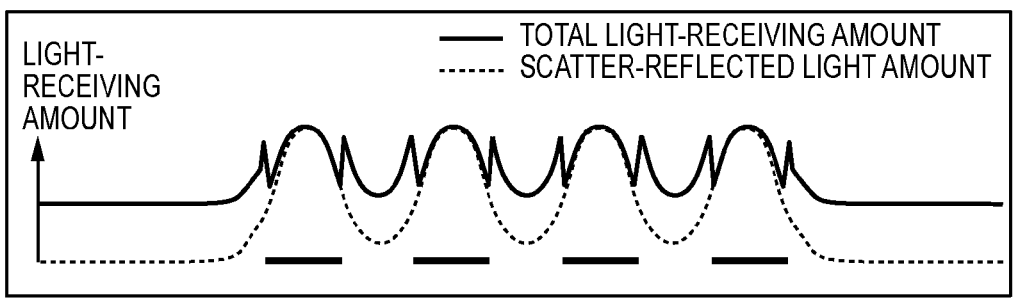

The scatter-reflected light components caused by the lines of the detection image 40 interfere with each other. The reflection state of the scatter-reflected light components of the entire detection image 40 is determined by the degree of interference. If the line pitch is large, and the space width is large, no even state is obtained even when the scatter-reflected light components interfere with each other, and an oscillating or varying state is obtained. The line pitch is the distance between the centers of adjacent lines, which equals the sum of the line width and the space width. For example, oscillation of the scatter-reflected light is very large when the line pitch is larger than in the state of FIG. 3C. In the state of FIG. 3D, the scatter-reflected light components of the lines scarcely interfere with each other. To the contrary, in the state of FIG. 3B, oscillation of the scatter-reflected light is very small. In the state of FIG. 3A, no oscillation occurs, and an almost even state is obtained. Note that the oscillation of the scatter-reflected light components changes depending on not only the line pitch but also the distance between the optical sensor 27 and the intermediate transfer belt 8. On the other hand, the specular-reflected light amount from the space portions of the detection image 40 oscillates in accordance with the line pitch. For this reason, the total light-receiving amount repetitively oscillates while being superimposed on the waveform of the scatter-reflected light indicated by the broken line.

Note that the lines shown in FIGS. 3A to 3D are formed at a density of almost 100%. When detecting the density, the lines are formed at a halftone density. In this case, although the scatter-reflected light components oscillate at the period of the line pitch, the oscillation amplitude value is smaller than that at the density of 100%. For example, when the density is 0%, the oscillation amplitude of the scatter-reflected light components is 0. When the density is 100%, the oscillation amplitude equals that in FIGS. 3A to 3D. When the density is the halftone density, an intermediate oscillation amplitude is obtained. That is, when the plurality of lines are formed under the condition that an almost predetermined amount of scatter-reflected light components is obtained at the density of 100%, an almost predetermined amount of scatter-reflected light components is obtained even at the halftone density.

A method of removing extracting scatter-reflected light components by a toner from the total light-receiving amount detected by the optical sensor 27 and extracting specular-reflected light components will be described next with reference to FIGS. 4A to 4C, 5A and 5B, and 6.

FIGS. 4A to 4C are explanatory views of processing for the photo-detection signal output from the optical sensor 27, and can mainly be used to detect the density. Note that FIGS. 4A to 4C illustrate both signals (left side of drawings) for the detection image 40 formed by toner of a color that generates a large amount of scatter-reflected light and signals (right side of drawings) for the detection image 40 formed by toner of a color that generates a small amount of scatter-reflected light. Note that the space width of the detection image 40, the distance between the optical sensor 27 and the intermediate transfer belt 8, and the like are adjusted such that the oscillation of the scatter-reflected light amount falls within a predetermined range.

FIG. 4A shows the photo-detection signal output from the optical sensor 27. In the detection image 40 of the color that generates a large amount of scatter reflection, the whole waveform is raised by the influence of the scatter-reflected light, as in FIG. 3A. In the detection image 40 of the color that generates a small amount of scatter reflection, since the irradiation light is absorbed by the toner, the waveform oscillates while being raised a little.

FIG. 4B shows a waveform obtained by, for example, setting two sections, obtaining a moving average value in each of the two sections, and further performing differential processing for the moving average values in the two sections. Note that the interval of the two sections is set to a predetermined period in which the phase of the photo-detection signal changes. For example, the interval is set to a period almost ½ the oscillation period of the photo-detection signal. As described above, the detection image 40 is formed such that the oscillation of the scattered light removed signal falls within a predetermined range. For this reason, the oscillation of the photo-detection signal shown in FIG. 4A is mainly the oscillation of the specular-reflected light amount. Hence, when differential processing for the two sections is performed, the scatter-reflected light components are removed or suppressed to a predetermined amount or less. That is, the signal shown in FIG. 4B is a scattered light removed signal obtained by removing the scattered light components from the total light-receiving amount. The amplitude of the scattered light removed signal indicates the line and space of the detection image, that is, the contrast of reflected light from the surface portion of the intermediate transfer belt 8, that is, the density information of the toner. For example, when the density of the line of the detection image 40 is lowered, the amplitude of the waveform shown in FIG. 4B becomes small.

FIG. 4C shows the amplitude value extracted from the scattered light removed signal in FIG. 4B, which can be used as density information. Note that since the scatter-reflected light component is not even near the start and end of detection of the detection image 40, the waveform is slightly distorted in the detection image 40 that generates a large amount of scatter reflection, as shown in FIG. 4B. If the amplitude value is extracted from the distorted waveform portion, an error occurs. To prevent this, the detection image 40 is made long to some extent in the sub-scanning direction, and a state in which the scatter-reflected light amount is even is ensured. When the scatter-reflected light component is even, the amplitude value can accurately be extracted from that portion. That is, it is possible to detect accurate density information.

Figure 5A:
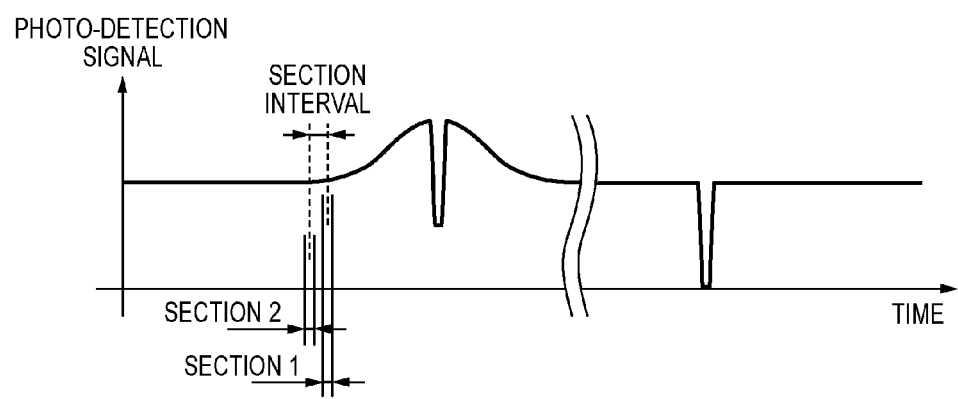
FIGS. 5A and 5B are explanatory views of processing for the detection image including one line according to an embodiment.
Figure 5B:
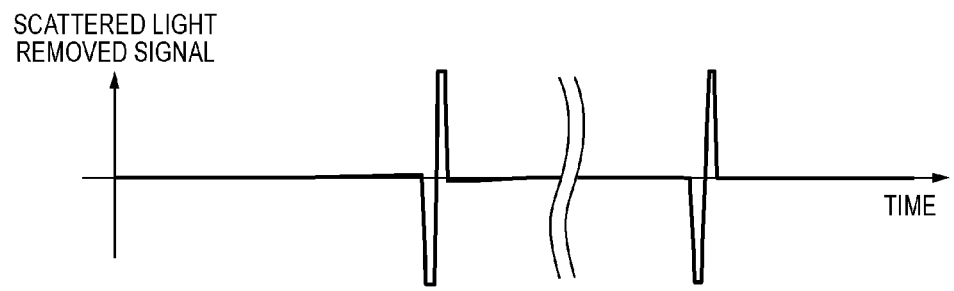

FIGS. 5A and 5B are explanatory views of a photo-detection signal when the detection image 40 including one line is used, unlike FIGS. 4A to 4C, and processing thereof. The detection image 40 including one line can be used to detect, for example, color misalignment. Note that like FIG. 4A, FIG. 5A illustrates both a case (left side of drawings) in which the detection image 40 is formed by toner of a color that generates a large amount of scatter-reflected light and a case (right side of drawings) in which the detection image 40 is formed by toner of a color that generates a small amount of scatter-reflected light. As shown in FIG. 5A, in the detection image 40 including one line, when the line has reached the position where the light-receiving element 277 receives specular-reflected light, the light-receiving amount attenuates. Note that as shown in FIG. 5A, when the scatter-reflected light amount is large, the light-receiving amount increases before and after the decrease in the specular-reflected light amount caused by the influence of the scatter-reflected light.

FIG. 5B shows a signal waveform obtained by providing two sections, obtaining a moving average value in each of the two sections, and further performing differential processing for the moving average values, as in the detection image 40 including a plurality of lines. In the signal waveform shown in FIG. 5B, the scatter-reflected light is almost removed, and correction to almost the same waveform is performed regardless of the amount of scatter reflection of the toner. In the detection image 40 including one line, the scatter-reflected light amount is not constant when the detection image 40 passes through the detection region of the optical sensor 27. For this reason, a small amount of scattered light components remains in the scatter-reflected light removed signal shown in FIG. 5B. This poses no problem when detecting the color misalignment amount because the object is to detect the passing timing of the detection image 40. However, to prevent the remaining scatter-reflected light components from being problematic, the width of time to cause the detection image 40 to pass through the detection region of the optical sensor 27 can be made much smaller than the width of time to detect the scatter-reflected light. When the signal shown in FIG. 5B is compared with a predetermined threshold, and timing data is generated, the arrival timing, that is, the position information of the detection image 40 can be detected. In this embodiment, the density information or position information of the detection image 40 of each color can be detected by the same processing regardless of the amount or presence/absence of scatter reflection of the toner. Note that even in the detection image 40 including a plurality of lines shown in FIG. 4A, the arrival timing can be detected by comparing the signal shown in FIG. 4B with a predetermined threshold.

FIG. 6 shows an exemplary detection system that performs the processes described with reference to FIGS. 4A to 4C and FIGS. 5A and 5B. The optical sensor 27 includes the light-receiving element 277 that detects reflected light from the intermediate transfer belt 8 and the detection image 40 on the intermediate transfer belt 8, and the processing circuit 275 that converts a current corresponding to the light-receiving amount output from the light-receiving element 277 into a voltage and outputs it as a photo-detection signal. A signal processing unit 28 is provided in the engine control unit 25 shown in FIG. 16, and includes a scattered light removing unit 30 that generates a scattered light removed signal by removing scatter-reflected light components from the photo-detection signal. The signal processing unit 28 also includes an amplitude data generation unit 50 that extracts the amplitude data of the scattered light removed signal, and a timing data generation unit 60 that generates the arrival timing data of the scattered light removed signal.

A sampling unit 31 in the scattered light removing unit 30 samples the photo-detection signal. Each of moving average processing units 32 and 33 calculates the moving average value in a section of the sampled photo-detection signal. More specifically, the moving average processing unit 32 calculates the moving average value in section 1 shown in FIG. 4A or 5A, and the moving average processing unit 33 calculates the moving average value in section 2 shown in FIG. 4A or 5A. A differential processing unit 34 performs a differential operation of the moving average values calculated by the moving average processing units 32 and 33, thereby generating a scattered light removed signal in which the scatter-reflected light components cancel each other so as to be removed or suppressed. Note that the interval between the sections in which the moving average processing units 32 and 33 calculate the moving average values is set to a value according to the pitch of the lines of the detection image 40 including a plurality of lines. For example, the sections can be set to sections including positions where the photo-detection signal has different amplitudes. For example, the interval between the two sections can be set such that the moving average processing unit 33 obtains the moving average in a section including the minimum value of the photo-detection signal in FIG. 4A while the moving average processing unit 32 obtains the moving average in a section including the maximum value of the photo-detection signal in FIG. 4A.

Note that although a form in which the difference between the moving averages in the two sections is obtained has been described above, the difference between the sum of the moving averages in a plurality of first sections and the sum of the moving averages in a plurality of second sections may be obtained. For example, the intervals between a total of six sections can be set such that the moving average in each of three second sections including different minimum values of the photo-detection signal is obtained while the moving average in each of three first sections including different maximum values of the photo-detection signal in FIG. 4A is obtained. That is, the sections can be set such that the photo-detection signals in the plurality of first sections are in phase, and the photo-detection signals in the plurality of second sections are in phase. Note that the number of sections, the length of each section, and the intervals between the sections can be set to various values other than those described above. However, a state capable of detecting the contrast generated by the presence/absence or density difference of the detection image 40 formed on the intermediate transfer belt 8 is basically set. In this embodiment, the simplest arrangement in which two sections are set will be exemplified. However, any other number of sections can be set.

The scattered light removed signal output from the scattered light removing unit 30 is input to the amplitude data generation unit 50 and the timing data generation unit 60. An amplitude detection unit 51 in the amplitude data generation unit 50 detects the amplitude value of the scattered light removed signal. The detected amplitude value of the scattered light removed signal is stored by an amplitude data management unit 52 and managed as data corresponding to the intensity of the reflected light from the detection image 40, for example, density information. A timing detection unit 61 in the timing data generation unit 60 detects the timing at which the scattered light removed signal exceeds a threshold. The detected timing data is position information corresponding to the formation position of the detection image 40, which can be handled as color misalignment information by managing the relative relationship of timing data with respect to the detection image 40 of each color.

For example, when the density information is fed back to the voltage condition of each bias or a process formation condition such as laser power, the maximum density or halftone characteristic of each color is corrected. In addition, when the scan start positions in the main scanning direction and sub-scanning direction and the image clock are adjusted for each color based on the color misalignment information, the color misalignment is corrected. Note that the lines include not only a solid line but also a discontinuous line such as a broken line or a dotted line, as described above. In the above-described embodiment, the line of the detection image 40 is perpendicular to the moving direction of the intermediate transfer belt 8. However, the line may be drawn, for example, obliquely with respect to the perpendicular direction. That is, the detection image 40 need only be an image whose toner amount (developing material amount) periodically changes in the moving direction of the intermediate transfer belt 8, and can include a line in a direction different from the moving direction of the detection image 40.

The optical sensor 27 according to this embodiment includes no converging mechanism of light. For this reason, the optical sensor can be downsized to a fraction of the conventional size, and can generate a signal in which the scattered light components from the detection image 40 are accurately removed. In addition, since no converging mechanism exists, the detection resolution can be increased without posing a problem by variations in the manufacture. Furthermore, since the detection resolution is high, the size of the image used to detect color misalignment or density can be made small.

Note that since the scatter-reflected light components are uneven at the ends of the detection image 40 that generates a large amount of scatter-reflected light, the waveform is slightly distorted, as shown in FIG. 4B. If the distortion of the waveform can be suppressed, the signal amplitude detection accuracy can be improved. A method of arranging two sections before and after section 1 and calculating the difference to improve the detection accuracy will be described below.

Figure 7A:
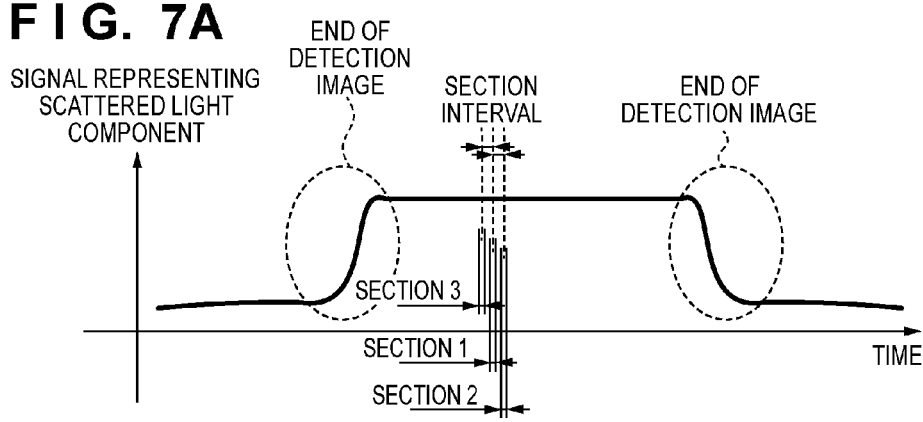
FIGS. 7A to 7C are explanatory views of scatter-reflected light removal according to an embodiment.

FIG. 7A shows the waveform of the scatter-reflected light component indicated by the dotted line in FIG. 3A. As the detection image 40 moves into the detection range of the optical sensor 27, the scatter-reflected light gradually becomes strong. In addition, as the detection image 40 moves out of the detection range of the optical sensor 27, the scatter-reflected light gradually becomes weak. Hence, the time-rate change in the received scatter-reflected light component exhibits a waveform having slopes at the ends, as shown in FIG. 7A.

Figure 7B:
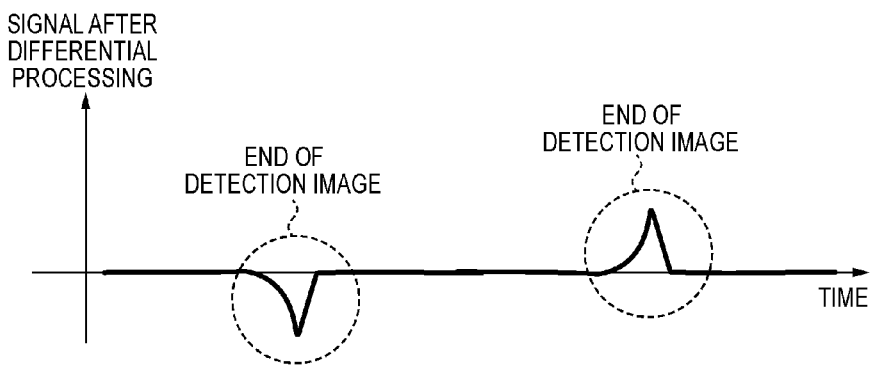

In this embodiment, as shown in FIG. 7A, section 2 is provided at a position earlier than section 1, and section 3 is provided at a position later than section 1. The difference between section 1 and sections 2 and 3 is calculated. Note that the concept for setting the time interval between section 1 and section 2 and that between section 1 and section 3 is the same as that for setting two sections. The time intervals may equal. FIG. 7B shows a waveform corresponding to the difference between the moving average values in the two sections 1 and 2 shown in FIG. 4A. The scatter-reflected light components increase or decrease at the ends of the detection image 40. For this reason, the scatter-reflected light components are not canceled by the difference between the two sections. Hence, the scattered light components remain even when differential processing is performed. Note that in FIG. 7B, the remaining scatter-reflected light components are exaggerated for the description.

Figure 7C:
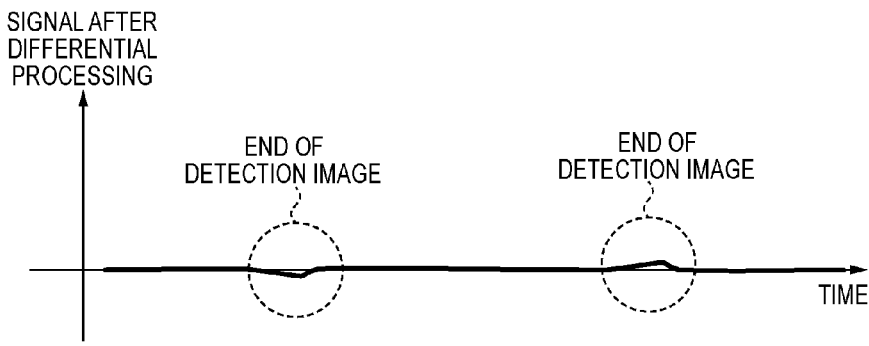
Figure 8A:
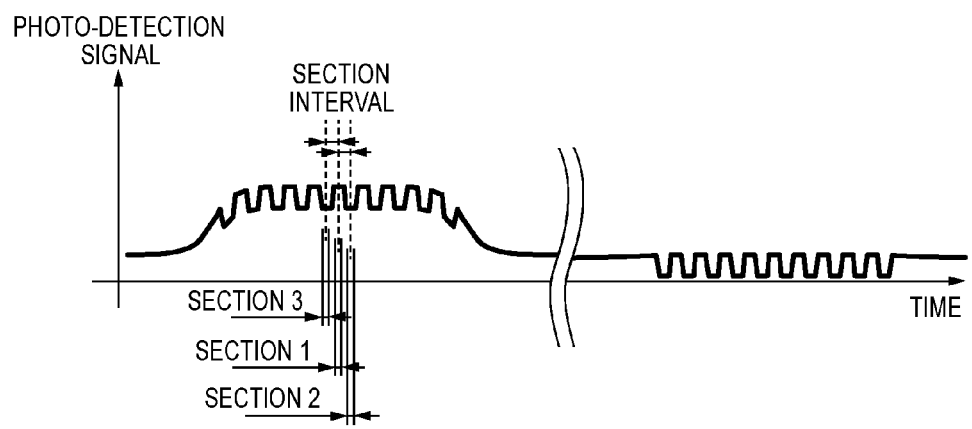
FIGS. 8A to 8C are explanatory views of processing for the detection image including a plurality of lines according to an embodiment.
Figure 8B:
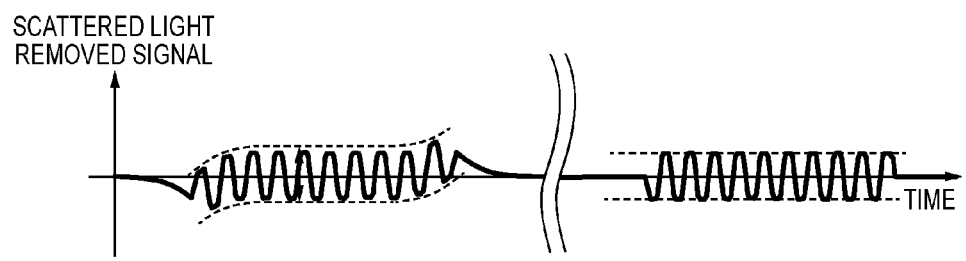
Figure 8C:
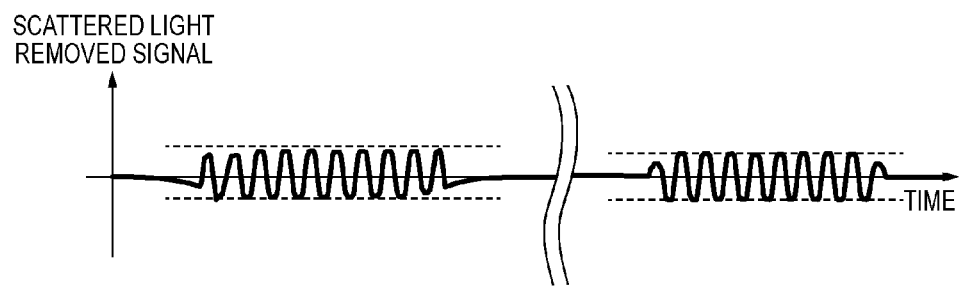

On the other hand, FIG. 7C shows the difference between the moving average value in section 1 and that in sections 2 and 3, as shown in FIG. 7A. Note that the moving average value in sections 2 and 3 indicates the average value between the moving average value in section 2 and that in section 3. As shown in FIG. 7C, when the two sections 2 and 3 are provided before and after section 1, the scatter-reflected light components in the moving average value of sections 2 and 3 almost equal those in the moving average value of section 1. For this reason, the remaining scatter-reflected light components can largely be suppressed. FIGS. 7A to 7C show only the scattered light components. FIGS. 8A to 8C show photo-detection signals corresponding to the total light-receiving amounts. The waveforms shown in FIGS. 8A and 8B are the same as those in FIGS. 4A and 4B. On the other hand, FIG. 8C shows a scattered light removed signal obtained by performing differential processing using the three sections shown in FIG. 8A. As is apparent from the waveform shown FIG. 8C, the scatter-reflected light components can largely be suppressed even at the ends of the detection image 40, as compared to the form shown in FIG. 8B in which the differential processing is performed using two sections. This suppresses the distortion of the waveform and improves the signal amplitude detection accuracy. It is therefore possible to more accurately detect the density of toner of each color using amplitude value information.

Note that even in a detection image of a color that generates a small amount of scatter reflection, the amplitude value (density value) can be detected by the same signal processing, as shown in FIG. 8C. That is, even in a state in which the amount of scatter reflection of toner is large or small, or scatter reflection of toner is uneven, the density information of the detection image 40 of each color can be detected by the same processing.

Figure 9A:
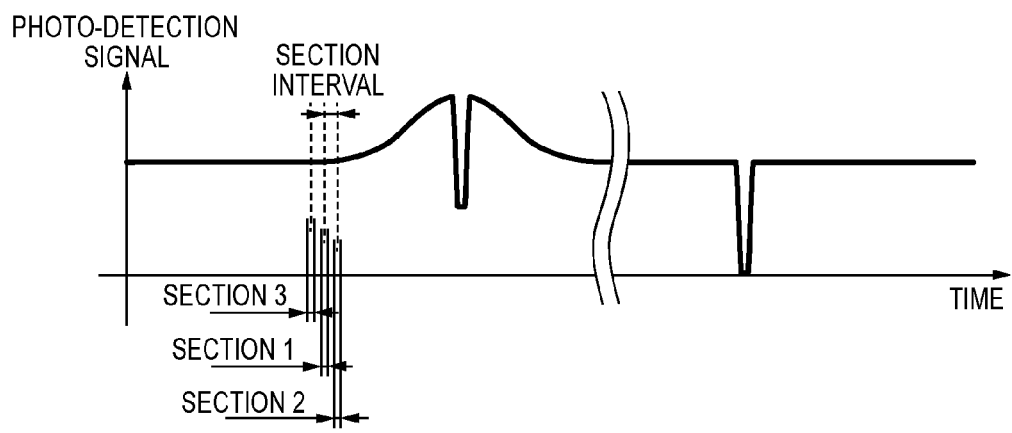
FIGS. 9A to 9C are explanatory views of processing for the detection image including one line according to an embodiment.
Figure 9B:
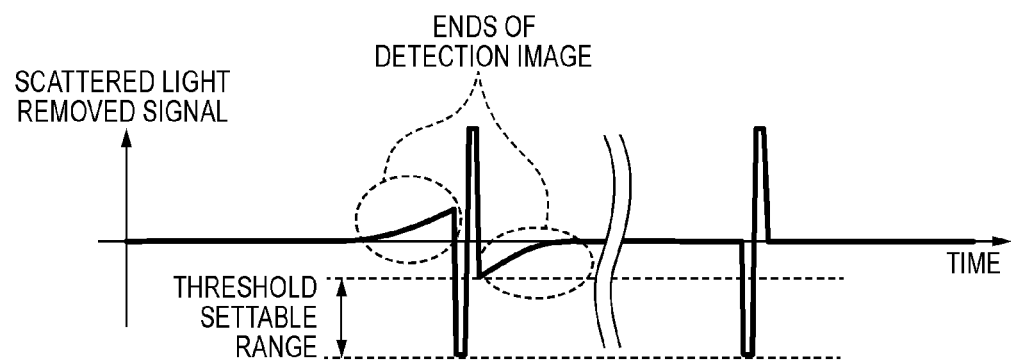

Additionally, suppressing the distortion of the signal waveform is also effective in detecting the position information, that is, the arrival timing of the detection image 40. FIG. 9A shows a waveform corresponding to FIG. 5A. FIG. 9B shows a waveform corresponding to FIG. 5B or a scattered light removed signal obtained by differential processing for sections 1 and 2 shown in FIG. 5A. Note that in FIG. 9B, the distortion of the waveform at the ends of the detection image 40, which is caused by the remaining scatter-reflected light components, is enhanced as compared to FIG. 5B. As shown in FIG. 9B, the threshold used to detect the position of the detection image 40 needs to be set while avoiding the distortion of the waveform. That is, if the distortion of the waveform becomes large, the threshold settable range narrows.

Figure 9C:
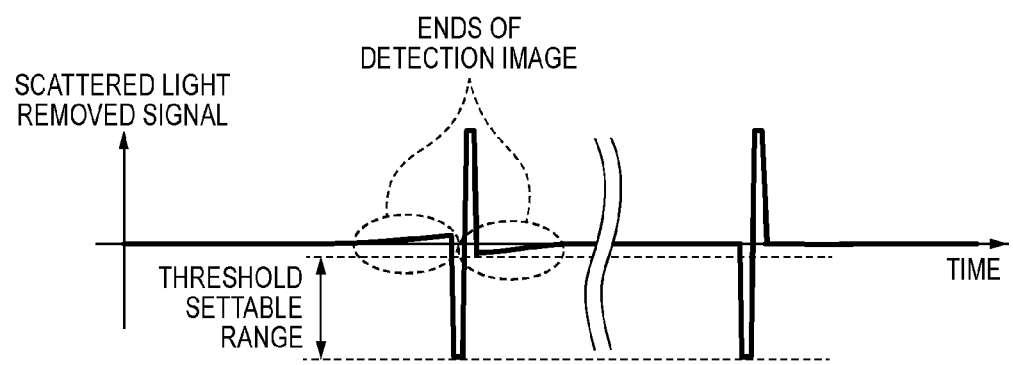

On the other hand, FIG. 9C shows the signal waveform of the difference between the moving average value in section 1 and that in sections 2 and 3 shown in FIG. 9A. When the moving average value in sections 2 and 3 provided before and after section 1 is obtained, the scatter-reflected light components are largely suppressed, and the distortion of the signal waveform is largely suppressed. When the distortion of the waveform is suppressed, the threshold setting range widens. It is therefore possible to reduce the possibility of detection errors caused by irregular noise or the like when acquiring the position information of the detection image 40.

As described above, a first section (section 1), and a second section (section 2) and a third section (section 3) located at positions earlier and later than the first section, respectively, are provided in the photo-detection signal. The difference between the moving average value in the first section and that in the second and third sections is obtained, thereby suppressing remaining scatter-reflected light regardless of its amount. As a result, the density of the detection image 40 can more accurately be detected. The position of the detection image can also more accurately be detected. Note that in the detection image 40 including one line, the narrower the line width is, the smaller the waveform distortion of the scattered light removed signal is. In addition, the longer the distance between the intermediate transfer belt 8 and the optical sensor 27 is, the smaller the waveform distortion of the scattered light removed signal is. Note that in the form in which three sections are provided, the detection system shown in FIG. 6 can be configured to cause the moving average processing unit 32 to obtain the moving average value in section 1 and the moving average processing unit 33 to obtain the moving average value in sections 2 and 3.

Note that in FIGS. 7A to 7C, 8A to 8C, and 9A to 9C, differential processing is performed between one first section and one second section and one third section. However, the three sections may make a set, and a plurality of sets may be provided. At this time, the second and third sections can be shared by another set. For example, the second section of the first set can be used as the third section of the second set earlier than the first set. In addition, since the average value in each section is used, the first to third sections need not always have the same width. For example, the second and third sections can be ½ the first section. This facilitates setting of causing the sections to belong to one set when making a set of three sections and providing a plurality of sets. Instead of obtaining the moving average values in the sections, the difference between the average value at a first time position and that at second and third time positions may be obtained while moving the three time positions. Note that the second time position is earlier than the first time position, and the third time position is later than the first time position. At this time, the time interval between the first time position and the second time position may equal that between the first time position and the third time position.

Second Embodiment

FIGS. 17A to 17D show the waveform of the scatter-reflected light component indicated by the dotted line in FIG. 3A. As already described, the time-rate change in the scatter-reflected light exhibits a waveform having slopes at the ends. Referring to FIGS. 17A to 17D, settings of sections to perform differential processing and a gap distance that is the distance between an intermediate transfer belt 8 and an optical sensor 27 are changed. FIGS. 17E to 17H show signals after differential processing using the sections shown in FIGS. 17A to 17D, respectively.

FIG. 17E shows a waveform obtained by calculating the moving average values in the two sections shown in FIG. 17A and performing differential processing or remaining scatter-reflected light components. At the ends of a detection image 40, the scatter-reflected light components are not even, and the waveform has slopes. Hence, the amount of remaining scatter-reflected light components is relatively large, as can be seen. Note that in FIGS. 17E to 17H, the remaining scatter-reflected light components are enhanced. FIG. 17F shows a waveform obtained by providing sections 2 and 3 before and after section 1, as shown in FIG. 17B, and performing differential processing for the moving average value in section 1 and that in sections 2 and 3. Note that the concept of the sections is the same as in the first embodiment. When two sections are set on both sides of section 1, and differential processing is performed, the remaining scatter-reflected light components can largely be suppressed even at the ends of the detection image 40. FIG. 17G shows a waveform obtained by performing differential processing for sections set as shown in FIG. 17C. Note that section setting in FIG. 17B and that in FIG. 17C are different only in the section interval. More specifically, a section interval TL between section 1 and each of sections 2 and 3 in FIG. 17C is longer than a section interval TS between section 1 and each of sections 2 and 3 in FIG. 17B. Note that the pitch between the lines of the detection image 40 has a value corresponding to the section interval. As is apparent from FIG. 17G, the narrower the line pitch of the detection image 40 is, the larger the effect of suppressing the scatter-reflected light components by differential processing is. FIG. 17H shows a waveform obtained by performing differential processing for sections set as shown in FIG. 17D. Note that FIGS. 17D and 17C are different only in the gap distance. The gap distance in FIG. 17D is longer than that in FIG. 17C. When the gap distance increases, scatter-reflected light is detected from a wider range. For this reason, the slopes at the leading and trailing edges of the detected waveform of the scatter-reflected light become moderate. This makes the effect of suppressing the scatter-reflected light components by differential processing large. Note that the form in which differential processing is performed for section 1 and the two sections on both sides, as shown in FIGS. 17B to 17D, instead of setting two sections as in FIG. 17A, will be referred to as a two-sided differential operation hereinafter. Note that in the two-sided differential operation, a moving average processing unit 32 shown in FIG. 6 obtains the moving average in section 1, and a moving average processing unit 33 obtains the moving average in each of sections 2 and 3 on both sides of section 1. Note that in this embodiment as in the first embodiment, one section 1, one section 2, and one section 3 may make a set, and a plurality of sets may be provided. The concept of set setting at this time is also the same as in the first embodiment.

The scatter-reflected light components removed by the two-sided differential operation largely change depending on the section setting method, the section interval, and the speed of rise/fall of the scatter-reflected light amount. For example, the section interval needs to be set in accordance with the line pitch of the detection image 40. In addition, since degree of slope of the rising/falling portions of the scatter-reflected light amount is decided by various conditions such as the density of the lines of the detection image 40 and the gap distance, a desired state cannot necessarily be obtained. That is, although the two-sided differential operation can enhance its effect by optimizing the line pitch of the detection image 40 and the arrangement of the optical sensor 27 within a possible range, it may be impossible to obtain a desired effect level due to the above-described constraints.

In such a case, even if the scatter-reflected light components remain, the signal amplitude extraction accuracy can be improved by extracting the signal amplitude only from a portion where no scatter-reflected light components remain.

FIG. 18A shows a detection image 41 including a plurality of lines formed by toner of a color that generates a large amount of scatter reflection. Note that the hollow arrow in FIG. 18A indicates the moving direction of the intermediate transfer belt 8. The detection image 41 includes a central portion 41a and portions 41b before and after it. Note that lines 41a-s and 41a-1 at the two ends of the central portion 41a are formed at the same density as the lines of the end portions 41b. The end portions 41b make the scatter-reflected light components almost even during the time when the optical sensor 27 is receiving specular-reflected light from the central portion 41a. Hence, when the signal amplitude is extracted based on the photo-detection signal during the time when the optical sensor 27 is receiving the specular-reflected light from the central portion 41a, the signal amplitude extraction accuracy can be improved. Note that the number of lines of the end portions 41b is decided by the line pitch, density, gap distance, and the like.

FIG. 18B shows a detection image 42 including a plurality of lines formed by toner of a color that generates a small amount of scatter reflection. Since the detection image 42 generates a small amount of scatter-reflected light components, the end portions 41b need not be provided, unlike the detection image 41.

The photo-detection signal shown on the left side of FIG. 19A is the signal obtained upon detecting the detection image 41, and the photo-detection signal shown on the right side is the signal obtained upon detecting the detection image 42. The scattered light removed signal shown in FIG. 19C is obtained by performing the two-sided differential operation for sections 1 to 3 set as shown in FIG. 19A. The photo-detection signal shown on the left side of FIG. 19B is the signal obtained upon detecting the detection image 41, and the photo-detection signal shown on the right side is the signal obtained upon detecting the detection image 42. Note that FIGS. 19A and 19B are different in the line pitch of the detection images 41 and 42. The line pitch is larger in FIG. 19B than in FIG. 19A.

In FIG. 19C, the scatter-reflected light components are almost removed even at the ends of the detection image 41. To the contrary, in FIG. 19D, the scatter-reflected light components are not removed at the ends of the detection image 41. Hence, the scattered light removed signal is distorted at the ends. In this case, the signal amplitude extraction accuracy can be improved by using only the portion shown in FIG. 19B where the specular-reflected light from the central portion of the detection image 41 is detected. Note that the entire region is usable in the detection image 42.

As described above, if the scatter-reflected light components remain even after the two-sided differential operation, the signal amplitude is extracted from a photo-detection signal portion corresponding to the specular-reflected light from the central portion without using the reflected light from the ends of the detection image 41, thereby improving the signal amplitude extraction accuracy. It is therefore possible to especially improve the density detection accuracy. Note that not the two-sided differential operation but the two sections shown in FIG. 17A may be used.

Third Embodiment

In this embodiment, a detection image 40 (to be referred to as a gradation detection image hereinafter) in which the line density is changed stepwise is used.

FIG. 10 shows a gradation detection image formed on an intermediate transfer belt 8. A line 81a of the gradation detection image shown in FIG. 10 has a density of 10%, a line 81b has a density of 20%, and a line 81c has a density of 30%. The density is thus increased in steps of 10%. Note that lines 81d, 81e, and 81f have densities of 80%, 90%, and 100%, respectively. Note that the step of 10% is merely an example, and lines that increase or decrease the density in an arbitrary step can be used.

Figure 11A:
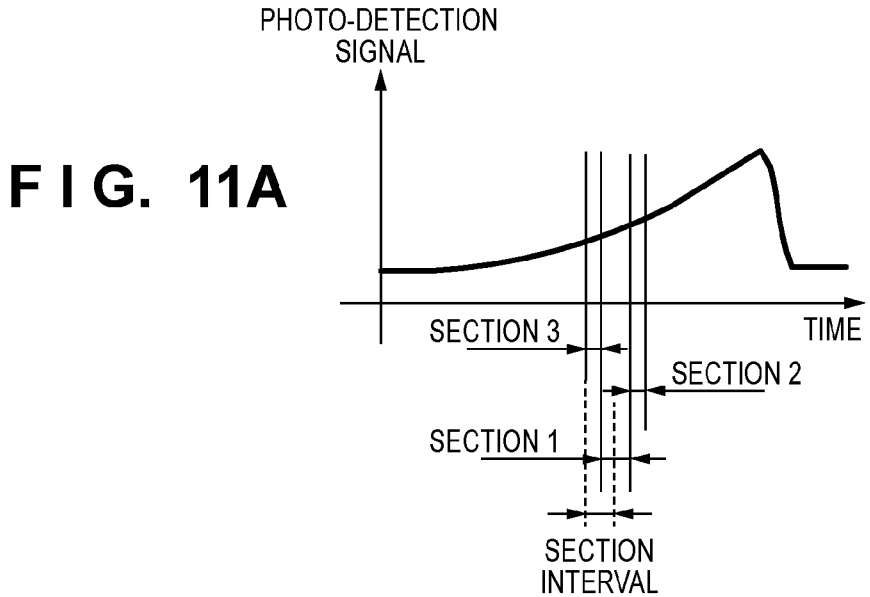
FIGS. 11A to 11C are explanatory views of scatter-reflected light removal in the detection image including the line of the plurality of halftone densities.

FIG. 11A shows a waveform representing scatter-reflected light components when the gradation detection image shown in FIG. 10 is detected by an optical sensor 27. The scatter-reflected light components gradually increase as the density of the gradation detection image rises. Note that since the increase amount increases toward the high density side, the slope gradually becomes large. Note that when the gradation detection image moves out of the detection range of the optical sensor 27, the scatter-reflected light decreases with a slope.

Figure 11B:
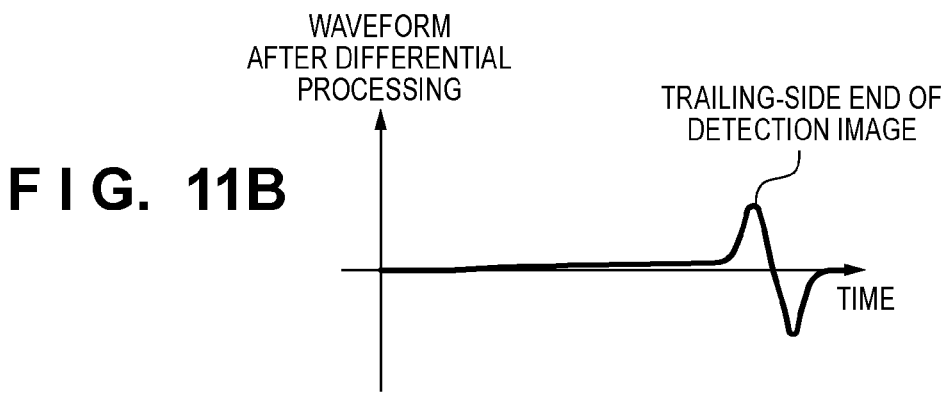

FIG. 11B shows a waveform when two sections are set, and moving average values are obtained. Due to the same reason as described in the first embodiment, a waveform distortion is caused by remaining reflected light components at the trailing-side end in the moving direction of the gradation detection image whose density largely changes. On the other hand, the density is low, and scatter-reflected light is small on the leading side in the moving direction of the gradation detection image. Hence, a waveform distortion occurs little due to the remaining scatter-reflected light components. However, as the density rises, the remaining scatter-reflected light components gradually increase. That is, in the waveform shown in FIG. 11B, the amplitude gradually becomes large toward the position where a waveform distortion occurs at the trailing-side end of the gradation detection image. As described above, when the gradation detection image is used, and differential processing is performed for two sections, a relatively large waveform distortion occurs at the end on the high density side. Even in the entire detection image, the waveform distortion occurs from the low density side to the high density side.

Figure 11C:
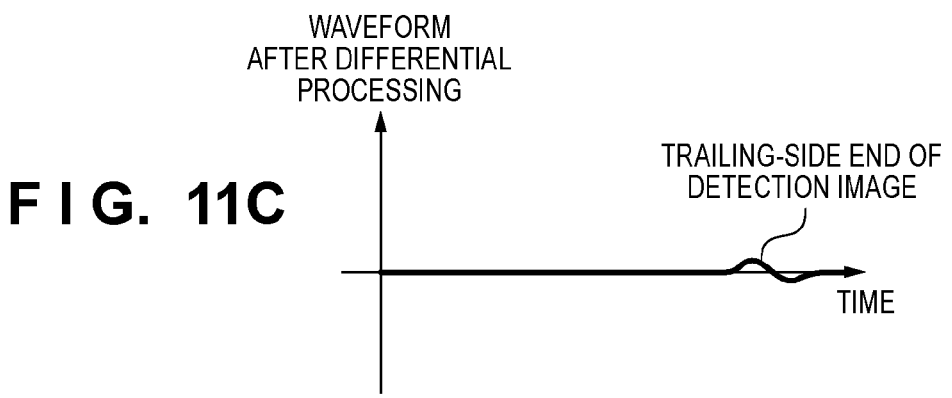

FIG. 11C shows a waveform obtained by performing differential processing for the moving average value in section 1 shown in FIG. 11A and the moving average value in sections 2 and 3. When differential processing is performed for section 1 and sections 2 and 3 provided before and after section 1, the scatter-reflected light components can effectively be suppressed even at the high density-side end of the gradation detection image.

Figure 12A:
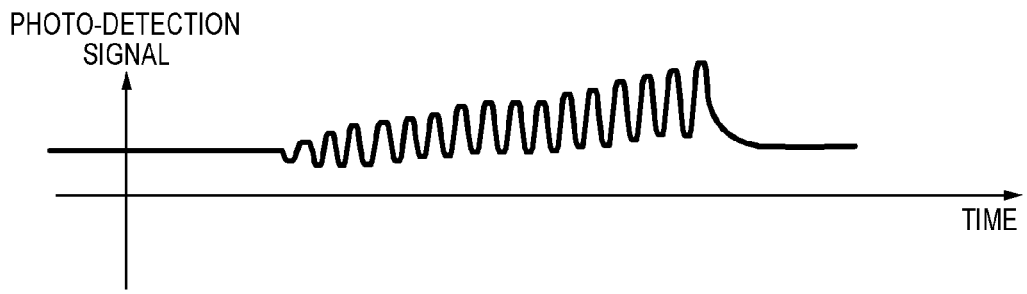
FIGS. 12A to 12C are explanatory views of processing for the detection image including the line of the plurality of halftone densities according to an embodiment.
Figure 12B:
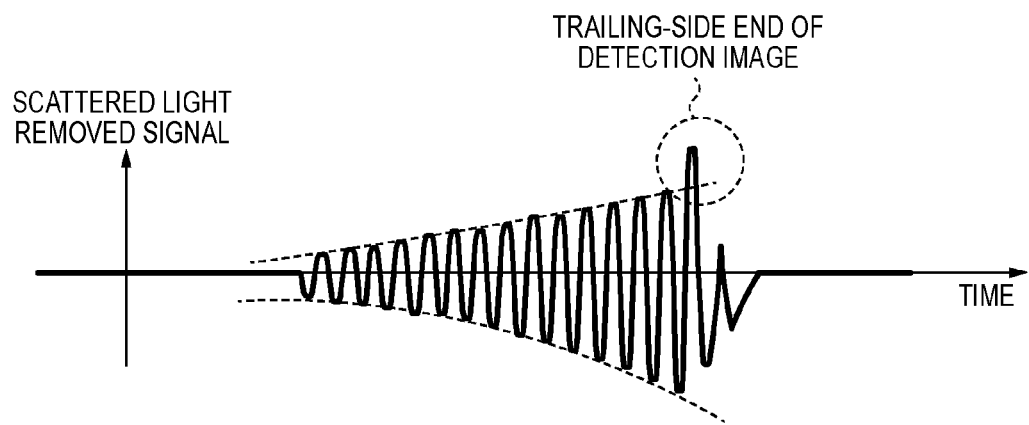
Figure 12C:
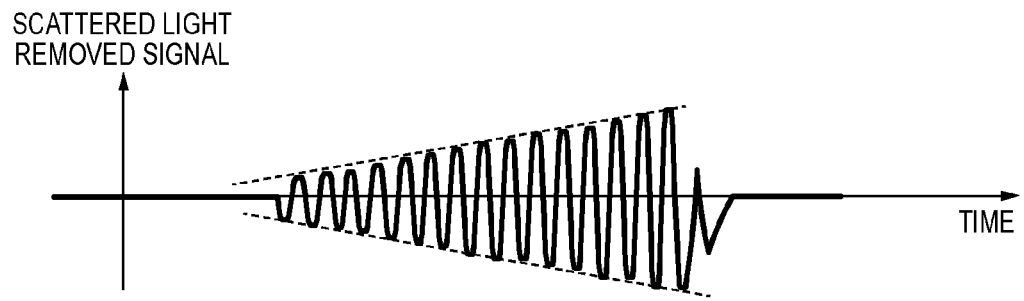

FIGS. 11A to 11C show only the scatter-reflected light components. FIGS. 12A to 12C show the photo-detection signal output from the optical sensor 27 and scattered light removed signals obtained by performing differential processing of the photo-detection signal. FIG. 12A shows the photo-detection signal obtained upon detecting the gradation detection image. FIG. 12B shows the scattered light removed signal obtained by performing differential processing using only two sections. FIG. 12C shows the scattered light removed signal obtained by performing differential processing for section 1 and sections 2 and 3 shown in FIG. 11A. In the waveform shown in FIG. 12B, since the scatter-reflected light components cannot completely be canceled, a relatively large waveform distortion occurs at the high density-side end of the detection image, and a waveform distortion also occurs in the entire detection image. On the other hand, in the signal waveform shown in FIG. 12C, since the slope state of the scatter-reflected light is canceled, the distortion of the signal waveform is largely suppressed. This improves the signal amplitude detection accuracy.

Fourth Embodiment

The fourth embodiment will be described next mainly concerning the difference from the second embodiment. In the second embodiment, the detection images 41 and 42 have the same line density. In the fourth embodiment, a detection image including lines of halftone densities that sequentially form a gradation stepwise is used, as in the third embodiment. FIG. 20A shows a detection image 43 formed by toner of a color that generates a large amount of scatter-reflected light. Note that the hollow arrow in FIG. 20A indicates the moving direction of an intermediate transfer belt 8. The detection image 43 is divided into a main body portion 43a on the leading side in the moving direction of the intermediate transfer belt 8, and a trailing-side end portion 43b on the trailing side. In the main body portion 43a of the detection image 43, a line 43a-s has the lowest density, and a line 43a-1 has the highest density. The trailing-side end portion 43b is provided not to abruptly decrease the scatter-reflected light at the time of detection of the main body portion 43a. Note that the density of the lines of the trailing-side end portion 43b is set not to be largely different from that of the line 43a-1. The number of lines of the trailing-side end portion 43b is decided by the line pitch, density, gap distance, and the like. FIG. 20B shows a detection image 44 formed by toner of a color that generates a small amount of scatter-reflected light. As for the densities of the lines of the detection image 44, the leftmost line in FIG. 20B has the lowest density, and the density gradually rises toward the right side of FIG. 20B.

Figure 21A:
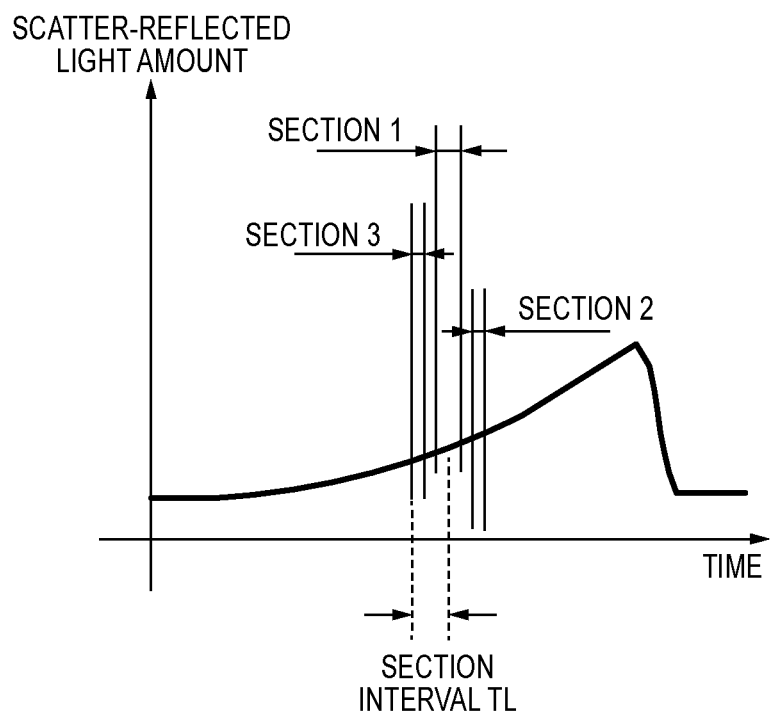
FIGS. 21A and 21B are explanatory views of differential processing according to an embodiment.

FIG. 21A shows the time-rate change in the scatter-reflected light components when the detection image 43 passes through the detection range of an optical sensor 27. The scatter-reflected light amount gradually increases as the line density rises. Since the increase amount increases toward the high density side, an arcuated curve is obtained, as shown in FIG. 21A. At the trailing-side end of the detection image 43, the scatter-reflected light amount decreases with a slope due to the same reason as in the second embodiment. Note that since the density is low at the leading-side end of the detection image 43, the scatter-reflected light components do not abruptly increase at the leading-side end of the detection image 43, unlike the second embodiment.

Figure 21B:
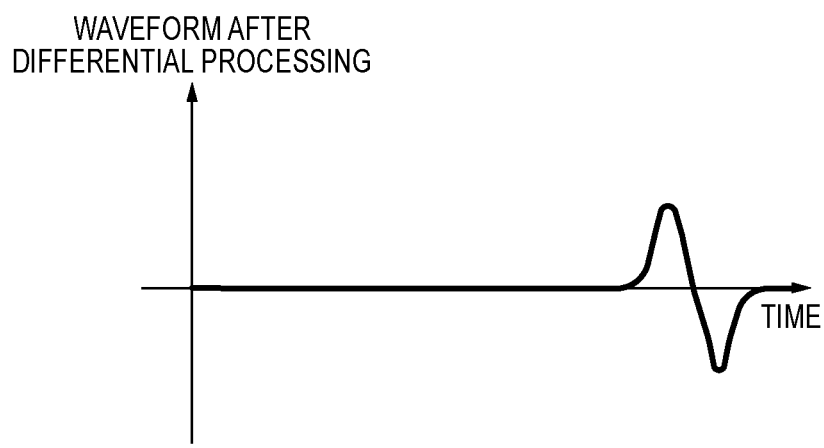

FIG. 21B shows scatter-reflected light components that remain when a two-sided differential operation is performed for sections set as shown in FIG. 21A. As shown in FIG. 21B, the scatter-reflected light components remain at the trailing-side end of the detection image 43. In this way, the scatter-reflected light components remain only at the high density-side end of the detection image 43. Note that if the high-density lines are formed on the leading side of the detection image 43, and the density is gradually lowered, the scatter-reflected light components remain at the leading-side end.

The photo-detection signal shown on the left side of FIG. 22A is the signal obtained upon detecting the detection image 43, and the photo-detection signal shown on the right side is the signal obtained upon detecting the detection image 44. The scattered light removed signal shown in FIG. 22B is obtained by performing the two-sided differential operation for sections 1 to 3 set as shown in FIG. 22A. The signal amplitude extraction accuracy can be improved by extracting the signal amplitude from the portion of the photo-detection signal corresponding to specular-reflected light from the main body portion except the high density-side end, in this example, the trailing-side end portion, as shown in FIG. 22B. It is therefore possible to especially improve the density detection accuracy. Note that in this embodiment as well, not the two-sided differential operation but differential processing of two sections may be used, as in the second embodiment.

Fifth Embodiment

In the first to fourth embodiments, reflected light from the intermediate transfer belt irradiated with divergent beams of a point source is detected using the single light-receiving element 277. In the fifth embodiment, the fact that use of a light-receiving element array including a plurality of light-receiving elements also makes it possible to reduce the influence of scatter-reflected light as in the first to fourth embodiments will be described. Note that the difference from the first embodiment will mainly be explained below, and a description of the same portions as in the first embodiment will be omitted.

FIGS. 13A to 13C are explanatory views of scatter-reflected light removal according to the first embodiment using a single light-receiving element 277. Note that the divergent beams of a point source are used as the irradiation light but not illustrated to avoid cumbersomeness. In FIGS. 13A to 13F, the solid lines indicate specular-reflected light, and the broken lines indicate scatter-reflected light. FIG. 13A shows a state in which the light-receiving element 277 receives specular-reflected light from a region B3 of an intermediate transfer belt 8. The light-receiving element 277 also receives scatter-reflected light from a detection image 40 arranged in a region B2. FIG. 13B shows a state in which the intermediate transfer belt 8 is then rotated, and a line of the detection image 40 has reached the reflection position of the specular-reflected light to the light-receiving element 277. The light-receiving element 277 hardly receives the specular-reflected light but receives the scatter-reflected light from the line arranged in the region B2. FIG. 13C shows a state in which the intermediate transfer belt 8 is further rotated, and the light-receiving element 277 receives the specular-reflected light from a region B1. In this state as well, the scatter-reflected light from the line in the region B2 is received. That is, the scatter-reflected light is received in all the states of FIGS. 13A to 13C. However, the specular-reflected light is not received in the state of FIG. 13B. Hence, the scatter-reflected light components can accurately be suppressed by subtracting the light-receiving amounts in the states of FIGS. 13A and 13C from the light-receiving amount in the state of FIG. 13B, as described in the first embodiment.

The fifth embodiment in which a light-receiving element array 280 including light-receiving elements 281, 282, and 283 will be described next. Referring to FIG. 13D, the light-receiving element 281 receives specular-reflected light from the region B3 of the intermediate transfer belt 8, and the light-receiving element 283 receives specular-reflected light from a region B5. On the other hand, the light-receiving element 282 hardly receives the specular-reflected light because of the line of the detection image located at the reflection position of the specular-reflected light. FIG. 13E shows a state in which the intermediate transfer belt 8 has moved from FIG. 13D. The light-receiving element 282 receives the specular-reflected light from the region B3 of the intermediate transfer belt 8. On the other hand, the light-receiving elements 281 and 283 hardly receive the specular-reflected light because of the lines of the detection image located at the reflection positions of the specular-reflected light to the light-receiving elements 281 and 283. In FIG. 13F, the intermediate transfer belt 8 further moves. The light-receiving elements 281 and 283 receive the specular-reflected light, although the light-receiving element 282 hardly receives the specular-reflected light.

Note that the light-receiving elements 281, 282, and 283 receive the scatter-reflected light from the detection image 40 in all the states of FIGS. 13D to 13F. As described above, when the surface of the intermediate transfer belt 8 moves, the light-receiving amount of each light-receiving element sequentially changes due to the lines of the detection image 40. In this embodiment, differential processing is performed at the same time position for the photo-detection signal output from the light-receiving element 282 and those from the light-receiving elements 281 and 283 arranged on both sides of the light-receiving element 282 in the moving direction of the detection image 40. This arrangement makes it possible to generate a signal by effectively removing the scatter-reflected light even at the ends of the detection image 40.

Figure 14:
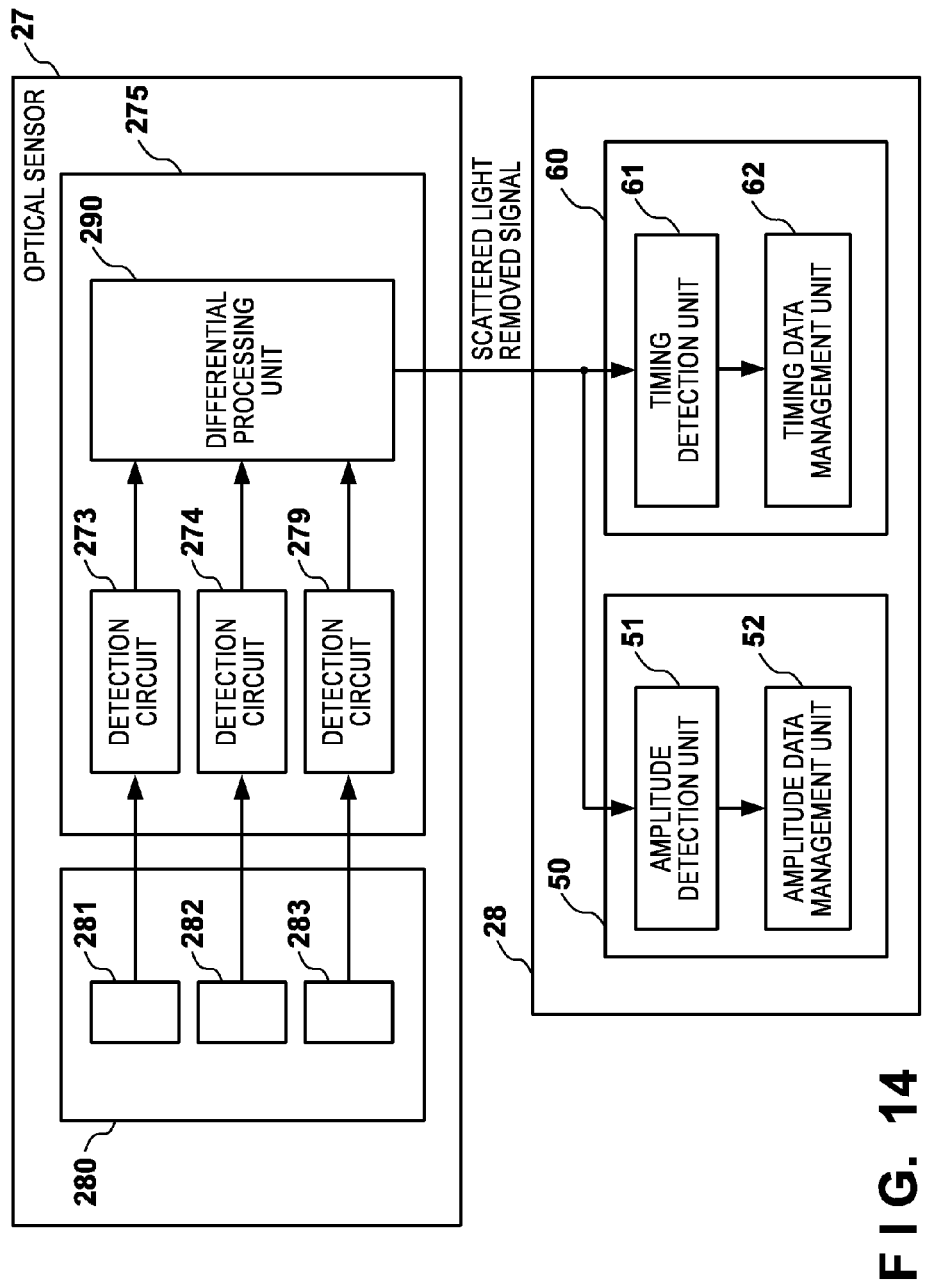
FIG. 14 is a block diagram showing the schematic arrangement of a detection system according to an embodiment.

FIG. 14 is a block diagram showing the schematic arrangement of a detection system according to this embodiment. As shown in FIG. 14, an optical sensor 27 of this embodiment includes the light-receiving element array 280. The light-receiving element array 280 includes the light-receiving elements 281, 282, and 283. Currents corresponding to the light-receiving amounts output from the light-receiving elements 281 to 283 are converted into photo-detection signals by detection circuits 273, 274, and 279 of a processing circuit 275, respectively, and output to a differential processing unit 290. The differential processing unit 290 generates a signal in which the scatter-reflected light components are removed by differential processing of the photo-detection signal from the detection circuit 274 and those from the detection circuits 273 and 279. Note that in this embodiment, the light-receiving elements 281 to 283 are arranged in the order of the light-receiving elements, 281, 282, and 283 along the moving direction of the surface of the intermediate transfer belt 8, that is, the sub-scanning direction. Note that although only one set of the light-receiving elements 281 to 283 is provided in this embodiment, a plurality of sets may be provided in the sub-scanning direction. In this case, the scattered light removed signal is the sum of signals obtained by differential processing of the respective sets. This arrangement corresponds to an arrangement for obtaining the difference between the sum of moving averages in a plurality of first sections and the moving averages in a plurality of second sections and a plurality of third sections in the first embodiment. In addition, if a plurality of sets are provided as described in the first embodiment, the light-receiving elements 281 and 283 can belong to both of adjacent sets. In this embodiment, the distance between the light-receiving elements 281 and 282 corresponds to the time interval between the first section and the second section in the first embodiment. Similarly, the distance between the light-receiving elements 282 and 283 corresponds to the time interval between the first section and the third section in the first embodiment.

As in the first embodiment, a signal processing unit 28 detects density information and position information for each color using the amplitude value information and timing information of the signal obtained by removing the scatter-reflected light. In this embodiment, the detection is performed using the plurality of light-receiving elements at the same timing for the specular-reflected light at different sub-scanning positions of the intermediate transfer belt 8. For this reason, the arrangement related to the signal processing and the like can be simple. Additionally, there is an advantage of monitoring the signal obtained by removing the scatter-reflected light from the detection image 40 in real time. Note that although a form using three light-receiving elements in correspondence with the two-sided differential operation has been explained, a form using two light-receiving elements may be used in correspondence with the form of the second embodiment in which differential processing of two sections is performed. In addition, a form that prohibits use of reflected light from the ends of a detection image formed by toner that generates a large amount of scattered light may be used in correspondence with the second embodiment.

Figure 15A:
FIGS. 15A to 15C are explanatory views of the relationship between the detection image and light-receiving elements according to an embodiment.
Figure 15B:
Figure 15C:

FIGS. 15A to 15C are explanatory views of the relationship between the lines of the detection image 40 and the light-receiving element array. Note that the lines shown in FIGS. 15A to 15C represent shadows generated by the lines of the detection image 40 at the position where the light-receiving element array is arranged. That is, the lines shown in FIGS. 15A to 15C indicate dark portions formed by the lines of the detection image 40. The regions between the lines shown in FIGS. 15A to 15C indicate bright portions formed by the spaces of the detection image 40. For example, assume that the optical path length from the light-emitting element to the detection image 40 equals that from the detection image 40 to the light-receiving element array. In this case, the actual line width and space width of the detection image 40 are ½ the widths of the dark and bright portions shown in FIGS. 15A to 15C. In FIG. 15A, the width of each dark/bright portion formed by the detection image 40 equals the length of the light-receiving region of each of the light-receiving elements 281, 282, and 283 in the moving direction of the intermediate transfer belt 8. The three light-receiving elements are arranged such that the light-receiving elements 281 and 283 are arranged on both sides of the light-receiving element 282 in the sub-scanning direction.

In FIG. 15B, the size of the light-receiving region of each light-receiving element is the same as in FIG. 15A, and the light-receiving elements are arranged at a distance. Referring to FIGS. 15A and 15B, the total size of the light-receiving regions of the light-receiving elements 281 and 283 is twice larger than the size of the light-receiving region of the light-receiving element 282. Note that when the main scanning direction length of each light-receiving element is assumed to be smaller than the main scanning direction length of each dark/bright portion formed by the detection image 40, the total sub-scanning direction width of the light-receiving regions of the light-receiving elements 281 and 283 is twice larger than the width of the light-receiving region of the light-receiving element 282. To cancel the scatter-reflected light components, the total light-receiving amount of the light-receiving elements 281 and 283 is divided by 2 to obtain the average value, and differential processing with respect to the light-receiving amount of the light-receiving element 282 is performed. That is, the signals to undergo the differential processing are obtained based on the same sub-scanning direction width of the light-receiving elements.

In FIG. 15C, the line width and space width are made larger than in FIG. 15A, and the sub-scanning direction width of the light-receiving region of the light-receiving element 282 is made equal to the total sub-scanning direction width of the light-receiving regions of the light-receiving elements 281 and 283. Note that in FIG. 15C, the width of the light-receiving region of each of the light-receiving elements 281 and 283 is ½ the sub-scanning direction width of the light-receiving region of the light-receiving element 282. For the light-receiving element arranged at the center and the two light-receiving elements arranged on both sides of it, the signals are corrected to those corresponding to the same sub-scanning direction width, and the differential processing is then performed. This makes it possible to cancel and remove the scatter-reflected light components. It is therefore possible to suppress the waveform distortion of the differential operation signal, which occurs at the ends of the detection image and the like, and generate a signal by more accurately removing the scatter-reflected light.

Note that in the first embodiment, differential processing is performed for different time positions of a signal representing the time-rate change in the light-receiving amount detected using one light-receiving element. With this processing, the difference in the reflected light amount including specular-reflected light components from different positions of the detection image 40 and the surface of the intermediate transfer belt 8 around it is obtained when the detection image 40 passes through the irradiation region of the light-emitting element 272. For example, in the first embodiment, assume that differential processing is performed for the value at the first time position of the detection signal and the average value at the second time position earlier than the first time position and the third time position later than the first time position. Note that in the first to third times, positions on the detection image 40, which are the reflection positions of the specular-reflected light to the light-receiving element 277, are defined as the first to third positions. In this case, the distance between the first position and the second position on the downstream side of the first position equals a value obtained by multiplying the moving speed of the surface of the intermediate transfer belt 8 by the difference between the first time and the second time. This also applies to the distance between the first position and the third position on the upstream side of the first position. Hence, performing differential processing for the first time position and the second and third time positions corresponds to performing differential processing for the total light-receiving amount upon receiving the specular-reflected light from the first position and the average value of the total light-receiving amounts upon receiving the specular-reflected light from the second and third positions. Note that the reflected light amount including the specular-reflected light components includes not only a state in which strong specular-reflected light is received from the spaces of the detection image 40 or the surface of the intermediate transfer belt 8 but also a state in which the light is scatter-reflected by the lines, and the amount of specular-reflected light components is zero or very small.

In the fifth embodiment, a plurality of, for example, three light-receiving elements are used, and differential processing is performed for signals representing the time-rate changes in the light-receiving amounts detected by the respective light-receiving elements at the same time position. With this processing, the difference in the reflected light amount including specular-reflected light components from different positions of the detection image 40 and the surface of the intermediate transfer belt 8 before and after it is obtained because the light-receiving elements cannot be arranged at the same position and are arranged at different positions. For example, in the fifth embodiment, assume that a second light-receiving unit and a third light-receiving unit are arranged on both sides of a first light-receiving unit in the sub-scanning direction, the first light-receiving unit outputs a first detection signal, the second light-receiving unit outputs a second detection signal, and the third light-receiving unit outputs a third detection signal. Note that the light-receiving regions of the light-receiving units have the same sub-scanning direction width. In a first time when the first light-receiving unit receives specular-reflected light from a first position of the detection image 40, positions on the detection image 40 or the surface of the intermediate transfer belt 8, which are the reflection positions of the specular-reflected light to the second and third light-receiving units, are defined as second and third positions. In this case, the distance between the first position and the second position is the distance corresponding to the distance between the first light-receiving unit and the second light-receiving unit. For example, if the optical path length from the light-emitting element to the detection image 40 equals that from the detection image 40 to the light-receiving unit, the distance between the first position and the second position is ½ the distance between the first light-receiving unit and the second light-receiving unit. This also applies to the first position and the third position. In this case, performing differential processing for the first detection signal and the average value of the second and third detection signals corresponds to performing differential processing for the light-receiving amount upon receiving the specular-reflected light from the first position and the average value of the light-receiving amounts upon receiving the specular-reflected light from the second and third positions. That is, in both the first and fifth embodiments, the difference in the reflected light amount including specular-reflected light components from different positions of the detection image 40 and the surface of the intermediate transfer belt 8 before and after it is obtained.

Note that since the light-receiving region of the light-receiving element is not a line in the main scanning direction and has a certain width in the sub-scanning direction as well, the light-receiving element simultaneously receives the specular-reflected light components from the certain sub-scanning direction width of the detection image 40 and the intermediate transfer belt 8. This corresponds to obtaining the average value of the light-receiving amounts in the sub-scanning direction. That is, in the first embodiment, differential processing is performed by obtaining the average values in the sections. The width of each section of the first embodiment corresponds to the sub-scanning direction length of the light-receiving region of the light-receiving element in the fifth embodiment. The section interval between the sections for which the differential processing is performed in the first embodiment corresponds to the sub-scanning direction arrangement interval between the light-receiving elements in the fifth embodiment.

In both the first and fifth embodiments, the differential processing can be regarded as differential processing performed while shifting the phase of the photo-detection signal. More specifically, the processing in the first embodiment is equivalent to branching one photo-detection signal into three signals, for example, giving no delay to the first photo-detection signal, a delay in a first amount to the second photo-detection signal, and a delay in an amount twice larger than the first amount to the third photo-detection signal, and performing differential processing. The first amount equals the section interval in the first embodiment. The differential processing can be performed not by simply shifting the phase but by performing moving average processing, as a matter of course. In the fifth embodiment, differential processing is performed for the photo-detection signals from the plurality of light-receiving units. Since the plurality of light-receiving units are arranged at different positions, the photo-detection signals from the plurality of light-receiving units are out of phase with each other. In this case, the phase difference corresponds to the distance between the arrangement positions of the light-receiving units.

Note that the above description also applies to the arrangement of the second embodiment in which the difference between two sections is obtained. That is, in the second embodiment, assume that differential processing is performed for the first time position of the detection signal and the second time position later than the first time position. Note that a position on the detection image 40, which is the reflection position of the specular-reflected light to the light-receiving element 277 in a first time, is defined as a first position, and a position on the detection image 40 or the surface of the intermediate transfer belt 8, which is the reflection position of the specular-reflected light to the light-receiving element 277 in a second time, is defined as a second position. In this case, the distance between the first position and the second position equals a value obtained by multiplying the moving speed of the surface of the intermediate transfer belt 8 by the difference between the first time and the second time. Hence, performing differential processing for the first time position and the second time position corresponds to performing differential processing for the total light-receiving amount when the light-receiving element 277 receives the specular-reflected light from the first position and the total light-receiving amount when the light-receiving element 277 receives the specular-reflected light from the second position.

In the fifth embodiment, assume that two light-receiving units, that is, the first light-receiving unit and the second light-receiving unit are arranged in the sub-scanning direction, the first light-receiving unit outputs the first detection signal, and the second light-receiving unit outputs the second detection signal. In a first time when the first light-receiving unit receives specular-reflected light from a first position of the detection image 40, a position on the detection image 40 or the surface of the intermediate transfer belt 8, which is the reflection position of the specular-reflected light to the second light-receiving unit, is defined as a second position. In this case, the distance between the first position and the second position is the distance corresponding to the distance between the first light-receiving unit and the second light-receiving unit. For example, if the optical path length from the light-emitting element to the detection image 40 equals that from the detection image 40 to the light-receiving unit, the distance between the first position and the second position is ½ the distance between the first light-receiving unit and the second light-receiving unit. In this case, performing differential processing for the values of the first detection signal and the second detection signal at the first time position corresponds to performing differential processing for the light-receiving amounts when the first light-receiving unit receives the specular-reflected light from the first position, and the second light-receiving unit receives the specular-reflected light from the second position. That is, in both the second and fifth embodiments, the difference in the reflected light amount including specular-reflected light components from different positions of the detection image 40 and the surface of the intermediate transfer belt 8 before and after it is obtained.

In both the second and fifth embodiments, the differential processing can be performed as differential processing performed while shifting the phase of the photo-detection signal. More specifically, the arrangement of the second embodiment in which differential processing is performed for the two sections is equivalent to branching one photo-detection signal into two signals, delaying one of the photo-detection signals by a predetermined amount, and performing differential processing. The predetermined amount to be delayed equals the section interval in the second embodiment. The differential processing can be performed not by simply shifting the phase but by performing moving average processing, as a matter of course. In the fifth embodiment, differential processing is performed for the photo-detection signals from the plurality of light-receiving units. Since the plurality of light-receiving units are arranged at different positions, the photo-detection signals from the plurality of light-receiving units are out of phase with each other. In this case, the phase difference corresponds to the distance between the arrangement positions of the light-receiving units.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-277445, filed on Dec. 19, 2012 and Japanese Patent Application No. 2012-277447, filed on Dec. 19, 2012, which are hereby incorporated by reference herein in their entirety.

The invention claimed is:

1. An image forming apparatus comprising:
an image carrier;
a forming unit configured to form a detection image made of a developing material on the image carrier;
an irradiation unit configured to irradiate the image carrier having the formed detection image with light;
a light-receiving unit configured to receive reflected light of the light irradiated by the irradiation unit and output a detection signal corresponding to a light-receiving amount of the reflected light including a specular-reflected light component; and
a detection unit configured to detect a first value of the detection signal corresponding to a first position of one of the detection image on the image carrier and a surface of the image carrier with the detection image formed thereon, a second value of the detection signal corresponding to a second position on a downstream side with respect to the first position in a moving direction of the detection image, and a third value of the detection signal corresponding to a third position on an upstream side with respect to the first position in the moving direction of the detection image during a time when the detection image formed on the image carrier passes through an irradiation region of the irradiation unit, and to detect one of position information and density information of the detection image based on a difference between the first value and an average value of the second value and the third value.

2. The apparatus according to claim 1, wherein the irradiation unit is further configured to irradiate the image carrier with divergent beams.

3. The apparatus according to claim 1, wherein the reflected light from the image carrier is received by the light-receiving unit without passing through an optical member configured to converge or condense the light.

4. The apparatus according to claim 1, wherein a distance between the first position and the second position equals a distance between the first position and the third position.

5. The apparatus according to claim 1, wherein an amount of the developing material of the detection image changes in the moving direction of the detection image, and
the distance between the image carrier and the light-receiving unit and the change in the amount of the developing material of the detection image are set such that an oscillation of an amount of scatter-reflected light received from the detection image by the light-receiving unit, which occurs due to movement of the detection image, is not more than a predetermined amount.

6. The apparatus according to claim 1, wherein the detection image includes a plurality of lines in a direction different from the moving direction of the detection image, and
the plurality of lines of the detection image have different densities.

7. The apparatus according to claim 1, wherein the detection image includes one line in a direction different from the moving direction of the detection image.

8. An image forming apparatus comprising:
an image carrier;
a forming unit configured to form a detection image made of a developing material on the image carrier;
an irradiation unit configured to irradiate the image carrier having the formed detection image with light;
a light-receiving unit configured to receive reflected light of the light irradiated by the irradiation unit and output a detection signal corresponding to a light-receiving amount of the reflected light including a specular-reflected light component; and
a detection unit configured to detect a first value of the detection signal corresponding to a first time position, a second value of the detection signal corresponding to a second time position earlier than the first time position of the detection signal, and a third value of the detection signal corresponding to a third time position later than the first time position of the detection signal, which are detected during a time when the detection image formed on the image carrier passes through an irradiation region of the irradiation unit, and to detect one of position information and density information of the detection image based on a difference between the first value and an average value of the second value and the third value.

9. The apparatus according to claim 8, wherein a time interval between the first time position and the second time position equals a time interval between the first time position and the third time position.

10. The apparatus according to claim 8, wherein the first value is an average value in a first section, the second value is an average value in a second section earlier than the first section, and the third value is an average value in a third section later than the first section.

11. The apparatus according to claim 8, wherein the detection image includes a plurality of lines in a direction different from a moving direction of the detection image, and
   an interval of the plurality of lines is such an interval that makes an oscillation of an amount of scatter-reflected light received from the detection image by the light-receiving unit, which occurs due to movement of the detection image, is not more than a predetermined amount.

12. The apparatus according to claim 1, wherein a position of an image to be formed is corrected using the position information, or a density of the image to be formed is corrected using the density information.

13. A detection apparatus comprising:
   an irradiation unit configured to irradiate an image carrier on which a detection image made of a developing material is formed with light;
   a light-receiving unit configured to receive reflected light of the light irradiated by the irradiation unit and output a detection signal corresponding to a light-receiving amount of the reflected light including a specular-reflected light component; and
   a detection unit configured to detect a first value of the detection signal corresponding to a first position of one of the detection image on the image carrier and a surface of the image carrier with the detection image formed thereon, a second value of the detection signal corresponding to a second position on a downstream side with respect to the first position in a moving direction of the detection image, and a third value of the detection signal corresponding to a third position on an upstream side with respect to the first position in the moving direction of the detection image during a time when the detection image formed on the image carrier passes through an irradiation region of the irradiation unit, and to detect one of position information and density information of the detection image based on a difference between the first value and an average value of the second value and the third value.

14. A detection apparatus comprising:
   an irradiation unit configured to irradiate an image carrier on which a detection image made of a developing material is formed with light;
   a light-receiving unit configured to receive reflected light of the light irradiated by the irradiation unit and output a detection signal corresponding to a light-receiving amount of the reflected light including a specular-reflected light component; and
   a detection unit configured to detect a first value of the detection signal corresponding to a first time position, a second value of the detection signal corresponding to a second time position earlier than the first time position of the detection signal, and a third value of the detection signal corresponding to a third time position later than the first time position of the detection signal, which are detected during a time when the detection image formed on the image carrier passes through an irradiation region of the irradiation unit, and to detect one of position information and density information of the detection image based on a difference between the first value and an average value of the second value and the third value.

* * * * *